US011807903B2

(12) United States Patent
Chen et al.

(10) Patent No.: US 11,807,903 B2
(45) Date of Patent: Nov. 7, 2023

(54) METHODS AND COMPOSITIONS FOR TRACKING NUCLEIC ACID FRAGMENT ORIGIN FOR NUCLEIC ACID SEQUENCING

(71) Applicant: Universal Sequencing Technology Corporation, Canton, MA (US)

(72) Inventors: Zhoutao Chen, Carlsbad, CA (US); Tsai-Chin Wu, San Marcos, CA (US); Long Kim Pham, San Diego, CA (US); Yong Wang, Sharon, MA (US)

(73) Assignee: Universal Sequencing Technology Corporation, Canton, MA (US)

( * ) Notice: Subject to any disclaimer, the term of this patent is extended or adjusted under 35 U.S.C. 154(b) by 338 days.

(21) Appl. No.: 16/968,576

(22) PCT Filed: Feb. 8, 2019

(86) PCT No.: PCT/US2019/017266
§ 371 (c)(1),
(2) Date: Aug. 8, 2020

(87) PCT Pub. No.: WO2019/157318
PCT Pub. Date: Aug. 15, 2019

(65) Prior Publication Data
US 2021/0047683 A1 Feb. 18, 2021

Related U.S. Application Data

(60) Provisional application No. 62/656,796, filed on Apr. 12, 2018, provisional application No. 62/628,079, filed on Feb. 8, 2018.

(51) Int. Cl.
*C12Q 1/68* (2018.01)
*C12Q 1/6869* (2018.01)
(Continued)

(52) U.S. Cl.
CPC ........ *C12Q 1/6869* (2013.01); *C12Q 1/6804* (2013.01); *C12Q 1/6834* (2013.01); *C12Q 1/6876* (2013.01)

(58) Field of Classification Search
CPC .................................................... C12Q 1/6869
See application file for complete search history.

(56) References Cited

U.S. PATENT DOCUMENTS 9,328,382 B2    5/2016  Drmanac et al.
2015/0353925 A1 12/2015 Grunenwald et al.
(Continued)

FOREIGN PATENT DOCUMENTS

WO    2017151828 A1    9/2017

OTHER PUBLICATIONS

Amini et al., "Haplotype-Resolved Whole Genome Sequencing by Contiguity Preserving Transposition and Combinatorial Indexing," Nature Genetics, Dec. 2014, vol. 46, No. 12, pp. 1343-1349.
(Continued)

*Primary Examiner* — Kenneth R Horlick
(74) *Attorney, Agent, or Firm* — Melissa Hunter-Ensor; Nathan Hsu; Greenberg Traurig, LLP

(57) ABSTRACT

The present disclosure provides methods and compositions for tracking nucleic acid fragment origin by target-specific barcode tagging when original nucleic acid targets break into small fragments. Nucleic acid targets are captured in vitro on a solid support with clonally localized nucleic acid barcode templates. Many nucleic acid targets canbe processed simultaneously in a massively parallel fashion without partition. These nucleic acid target tracking methods can be used for a variety of applications in both whole genome sequencing and targeted sequencing in order to accurately identify genomic variants, haplotype phasing and assembly, for example.

40 Claims, 20 Drawing Sheets

(51) Int. Cl.
  *C12Q 1/6804* (2018.01)
  *C12Q 1/6834* (2018.01)
  *C12Q 1/6876* (2018.01)

(56) References Cited

U.S. PATENT DOCUMENTS

| | | | |
|---|---|---|---|
| 2016/0046985 A1* | 2/2016 | Drmanac | C12Q 1/6806 506/4 |
| 2016/0177359 A1 | 6/2016 | Ukanis et al. | |
| 2016/0289669 A1 | 10/2016 | Fan et al. | |
| 2016/0369266 A1* | 12/2016 | Belyaev | C12N 15/1065 |
| 2019/0078150 A1* | 3/2019 | Chen | C12Q 1/6876 |
| 2022/0298545 A1* | 9/2022 | Chen | C12Q 1/6876 |

OTHER PUBLICATIONS

Au et al., "True Reversal of Mu Integration," The EMBO Journal, 2004, vol. 23, No. 16, pp. 3408-3420.
Bankevich et al., "SPAdes: A New Genome Assembly Algorithm and Its Applications to Single-Cell Sequencing," Journal of Computational Biology, 2012, vol. 19, No. 5, pp. 455-477.
Bankevich et al., "TruSPAdes: Barcode Assembly of TruSeq Synthetic Long Reads," Nature Methods, Mar. 2016, vol. 13, No. 3, pp. 248-250.
Boeke, J., Transposable elements in *Saccharomyces cerevisiae*, pp. 335-374 in Mobile DNA edited by D.E. Berg & M. M. Howe. American Society for Microbiology, Washington USA, 1989.
Burton et al., "Mu Transpososome Architecture Ensures That Unfolding by ClpX or Proteolysis by ClpXP Remodels but Does Not Destroy the Complex," Chemistry & Biology, May 2003, vol. 10, No. 5, pp. 463-472.
Chen et al., "Ultralow-Input Single-Tube Linked-Read Library Method Enables Short-Read Second-Generation Sequencing Systems to Routinely Generate Highly Accurate and Economical Long-Range Sequencing Information," Genome Research, 2020, vol. 30, No. 6, pp. 898-909.
Craig et al., "Transposon Tn7," Transposable Elements, Current Topics in Microbiology and Immunology, 1996, vol. 204, pp. 27-48.
Crouse et al., "Ethanol Precipitation: Ammonium Acetate as an Alternative to Sodium Acetate," Focus, 1987, vol. 9, No. 2, pp. 3-5.
Devine et al., "Efficient Integration of Artificial Transposons into Plasmid Targets in Vitro: A Useful Tool for DNA Mapping, Sequencing and Genetic Analysis.," Nucleic Acids Research, 1994, vol. 22, No. 18, pp. 3765-3772.
Diehl et al., "Detection and Quantification of Mutations in the Plasma of Patients with Colorectal Tumors," Proceedings of the National Academy of Sciences, Nov. 8, 2005, vol. 102, No. 45, pp. 16368-16373.
Edge et al., "HapCUT2: Robust and Accurate Haplotype Assembly for Diverse Sequencing Technologies," Genome Research, 2017, vol. 27, No. 5, pp. 801-812.
Haapa et al., "An Efficient and Accurate Integration of Mini-Mu Transposons in Vitro: A General Methodology for Functional Genetic Analysis and Molecular Biology Applications," Nucleic Acids Research, 1999, vol. 27, No. 13, pp. 2777-2784.
Ichikawa et al., "In Vitro Transposition of Transposon Tn3.," Journal of Biological Chemistry, Nov. 5, 1990, vol. 265, No. 31, pp. 18829-18832.
Kaufman et al., "P Element Transposition in Vitro Proceeds by a Cut-and-Paste Mechanism and Uses GTP as a Cofactor," Cell, Apr. 3, 1992, vol. 69, No. 1, pp. 27-39.
Kestin et al., "Viscosity of Liquid Water in the Range −8 ° C to 150 ° C," Journal of Physical and Chemical Reference Data, 1978, vol. 7, No. 3, pp. 941-948.
Kleckner et al., "Tn10 and IS10 Transposition and Chromosome Rearrangements: Mechanism and Regulation In Vivo and In Vitro," Transposable Elements, Current Topics in Microbiology and Immunology, 1996, pp. 49-82.
Lampe et al., "A Purified Mariner Transposase is Sufficient to Mediate Transposition in Vitro.," The EMBO Journal, 1996, vol. 15, No. 19, pp. 5470-5479.
Lis et al., "Size Fractionation of Double-Stranded DNA by Precipitation with Polyethylene Glycol," Nucleic Acids Research, Mar. 1975, vol. 2, No. 3, pp. 383-389.
Macosko et al., "Highly Parallel Genome-Wide Expression Profiling of Individual Cells Using Nanoliter Droplets," Cell, May 21, 2015, vol. 161, No. 5, pp. 1202-1214.
Mizuuchi et al., "Assembly of the Active Form of the Transposase-Mu DNA Complex: A Critical Control Point in Mu Transposition," Cell, Jul. 24, 1992, vol. 70, No. 2, pp. 303-311.
Ohtsubo et al., "Bacterial Insertion Sequences," Transposable Elements, Current Topics in Microbiology and Immunology, 1996, vol. 204, pp. 1-26.
Park et al., "In Vitro Transposition of Tn5," The Journal of the Korean Society for Microbiology, Aug. 1992, vol. 27, No. 4, pp. 381-389.
Pelta et al., "DNA Aggregation Induced by Polyamines and Cobalthexamine (?)," Journal of Biological Chemistry, Mar. 8, 1996, vol. 271, No. 10, pp. 5656-5662.
Savilahti et al., "The Phage Mu Transpososome Core: DNA Requirements for Assembly and Function.," The EMBO Journal, 1995, vol. 14, No. 19, pp. 4893-4903.
Surette et al., "Transpososomes: Stable Protein-DNA Complexes Involved in the in Vitro Transposition of Bacteriophage Mu DNA," Cell, Apr. 24, 1987, vol. 49, No. 2, pp. 253-262.
Varmus et al., "Retroviruses," Mobile DNA, 1996, Berg DE and Howe M. Eds. American Society for Microbiology, Washington DC, pp. 53-108.
Vos et al., "Transposase is the Only Nematode Protein Required for in Vitro Transposition of Tc1.," Genes & Development, 1996, vol. 10, No. 6, pp. 755-761.
Zhang et al., "Haplotype Phasing of Whole Human Genomes Using Bead-Based Barcode Partitioning in a Single Tube," Nature Biotechnology, Sep. 2017, vol. 35, No. 9, pp. 852-857.
Zheng et al., "Haplotyping Germline and Cancer Genomes with High-Throughput Linked-Read Sequencing," Nature Biotechnology, Mar. 2016, vol. 34, No. 3, pp. 303-311.
International Search Report for International Application No. PCT/US19/17266, dated May 23, 2019, 4 pages.

\* cited by examiner

METHODS AND COMPOSITIONS FOR TRACKING NUCLEIC ACID FRAGMENT ORIGIN FOR NUCLEIC ACID SEQUENCING

This patent application is a United States 371 National Phase Application of International Patent Cooperation Treaty Application No. PCT/US2019/17266, with an International Filing Date of Feb. 8, 2019, which claims the priority of provisional filings U.S. 62/628,079, filed on Feb. 8, 2018 and U.S. 62/656,796, filed on Apr. 12, 2018. They are included in here in their entirety. All publications, patents and other documents mentioned herein are incorporated by reference in their entirety.

FIELD

The present invention relates in general to methods and compositions for nucleic acid sequencing. In particular, the methods and compositions provided herein are related to preparation of nuclei acid library and generation of sequencing data therefrom.

BACKGROUND

Nucleic acid sequencing can provide information for a wide variety of biomedical applications, including diagnostics, prognostics, pharmacogenomics, and forensic biology. Sequencing may involve basic low throughput methods including Maxam-Gilbert sequencing (chemically modified nucleotide) and Sanger sequencing (chain-termination) methods, or high throughput next-generation methods including massively parallel pyrosequencing, sequencing by synthesis, sequencing by ligation, semiconductor sequencing, and others. For most sequencing methods, a sample, such as a nucleic acid target, needs to be processed into a sequencing library prior to be sequenced on a sequencing instrument. For example, a sample may be fragmented, amplified or attached to an identifier. Unique identifiers are often used to identify the origin of a particular sample.

Most commercially available sequencing technologies have limited sequencing read length. Second generation sequencing technologies particularly can sequence only several hundred bases and hardly reach a thousand bases. However, nucleic acid sequences of a gene can span from several kilobases to tens and hundreds of kilobases, which means sequencing read length of tens of kilobases is necessary to successfully determine the haplotypes of all genes.

To overcome the short sequencing read length problem, many methods have been developed to target-specifically label long nucleic acid targets when they are broken into small fragments for sequencing library preparation. Such methods include Complete Genomics's long fragment read, Illumina's synthetic long read, 10× Genomics's linked-read (Zheng et al, 2016), Illumina's single tube method (Zhang et al, 2017) and our own single tube method (WO2017/151828). These target-specific labels are short nucleic acid sequences, called barcodes. The origin of these short nucleic acid fragments can be identified based on their unique, associated barcode. The broader diversity of a barcode population used in the method, the better specificity it provides for identification. 10× Genomics's linked-read method has been used widely. However, it requires a water-in-oil emulsion method to keep the clonality of target-specific barcode labelling reaction. This requirement significantly increases the complexity of its sample preparation procedure and cost. Several methods, including the method belonging to Complete Genomics (U.S. Pat. No. 9,328,382), Illumina's single tube method (Zhang et al, 2017) and our method (WO2017/151828) use transposase-based system and remove the need of partition of nucleic acid targets with emulsion droplets in the reaction. These methods enable target-specific barcoding in a single tube reaction format in principle. The present invention provides novel transposase based single tube barcoding methods with significant improvement on reaction efficiency and simplicity of the workflow.

SUMMARY

In one aspect, described herein are methods of tracking nucleic acid fragment origin by barcode tagging. The methods include providing a ligase, a plurality of solid support having clonal barcode templates or semi-clonal barcode templates immobilized thereon, and a plurality of transpososomes, each transpososome comprising transposable DNA and transposase, wherein at least one transposable DNA in the transpososome is capable of ligating to the barcode template on the solid support directly or indirectly. A nucleic acid target contacts the ligase, the solid support, and the transpososomes in one reaction vessel to attach the barcode information on the solid support to the nucleic acid target by simultaneous strand transfer and ligation reactions. The nucleic acid target is broken into fragments by breaking strand transfer complexes, wherein at least one fragment is attached to a barcode template on the solid support.

In one aspect, described herein are methods of tracking nucleic acid fragment origin by barcode tagging. The methods include providing a plurality of solid support having clonal barcode templates or semi-clonal barcode templates immobilized thereon, and a plurality of transpososomes, each transpososome comprising transposable DNA and transposase, wherein at least one transposable DNA in the transpososome is capable of being captured by the barcode template on the solid support directly or indirectly by hybridization or an affinity moiety. A nucleic acid target contacts the solid support, and the transpososomes in one reaction vessel to attach the barcode information on the solid support to the nucleic acid target by simultaneous strand transfer and capture reactions. The aforementioned reaction occurs at substantially the same time without additional partition of each nucleic acid target from another nucleic acid target within the total plurality of nucleic acid targets. The nucleic acid target is broken into fragments by breaking strand transfer complexes, wherein at least one fragment is attached to a barcode template on the solid support.

In some instances, the clonal barcode templates or semi-clonal barcode templates immobilized on the solid support are produced by methods of direct synthesis, clonal amplification, or a combination thereof. The clonal amplification can be emulsion PCR, bridge PCR, isothermal PCR, template walking, nanoball generation, and a combination thereof. In particular instances, the barcoded solid support is prepared by a clonal amplification method without separating amplified and unamplified populations. Further instances, the barcoded solid support is prepared by a clonal amplification with only or predominantly enriched amplified populations.

In one aspect, the reactions are in a buffer system with a controlled viscosity to decrease diffusion and increase suspension by adding substance selected from the group of polyethylene glycol, pluronic, cellulose, agarose, and their derivatives, and other polymers, and a combination thereof, with a viscosity at about 1-200 mPas at temperature of approximately 20° C., preferably 1.5-30 mPas at temperature of approximately 20° c.

In one aspect, the transpososomes can be replaced with individual transposable DNAs and transposases without pre-assembling them into transpososomes.

In another aspect, a second transpososome is added after the initial reaction in the reaction vessel; wherein the previously added transpososome is referred to as the first transpososome, and the first and second transpososomes can be of the same type or different type, or different transposon sequences of the same type. In another aspect, a second transpososome is added after breaking the nucleic acid target into fragments.

In another aspect, the nucleic acid target can be pre-attached to the solid support by non-specific binding.

In another aspect, the capture reaction in the vessel is by ligation, or by hybridization, or by affinity tag, or by antibody and antigen reaction, or by click chemistry, or a combination thereof.

In another aspect, the capture reaction comprises first hybridization andthen ligation.

In another aspect, the barcoded solid support has transposable DNAs or transpososomes pre-attach to the end of some barcode templates immobilized on the solid support.

In another aspect, said transposase is selected from the group consisting of Tn, Mu, Ty, and Tc transposases in a wildtype, a mutant or a tagged version thereof, and a combination thereof. In particular, the transposase is a MuA transposase, or a Tn5 transposase in a wildtype or a mutant or a tagged version thereof, or a combination thereof.

In another aspect, said transposable DNA contains a transposon, wherein the transposon is selected from the group consisting of Tn, Mu, Ty, and Tc transposon DNAs in a wildtype or a mutant version thereof, and a combination thereof. In particular, said transposon is a MuA transposon, or a Tn5 transposon, wild type or mutant, or a combination thereof.

In another aspect, said transposable DNA further comprises an adaptor sequence.

In another aspect, said transposable DNA capable of being captured by said barcode template has no complementary sequences to said barcode template, and the capture of said transposable DNA to said barcode template is facilitated by a linker.

In another aspect, said transpososome comprises at least one type of transposase, at least one type of transposable DNA or a combination thereof.

In one aspect, described herein are methods of tracking nucleic acid fragment origin by barcode tagging. The methods include providing a ligase, a plurality of solid support having clonal barcode templates or semi-clonal barcode templates immobilized thereon and capturing a nucleic acid target to the solid support via non-specific binding, and providing a plurality of transpososomes, each transpososome comprising transposable DNA and transposase, wherein at least one transposable DNA in the transpososome is capable of ligating to the barcode template on the solid support directly or indirectly. Contact the non-specifically bound nucleic acid target on the solid support with the ligase and the transpososomes in one reaction vessel to attach the barcode information on the solid support to the nucleic acid target by simultaneous strand transfer and ligation reactions. The nucleic acid target is broken into fragments by breaking strand transfer complexes, wherein at least one fragment is attached to a barcode template on the solid support.

In one aspect, described herein are methods of tracking nucleic acid fragment origin by barcode tagging. The methods include providing a plurality of solid support having clonal barcode templates or semi-clonal barcode templates immobilized thereon and capturing a nucleic acid target to the solid support via non-specific binding, and providing a plurality of transpososomes, each transpososome comprising transposable DNA and transposase, wherein at least one transposable DNA in the transpososome is capable of being specifically captured to the barcode template on the solid support directly or indirectly. Contact the non-specifically bound nucleic acid target on the solid support with the transpososomes in one reaction vessel to attach the barcode information on the solid support to the nucleic acid target by simultaneous strand transfer and capture reactions. The nucleic acid target is broken into fragments by breaking strand transfer complexes, wherein at least one fragment is attached to a barcode template on the solid support.

In one aspect, described herein are methods of tracking nucleic acid fragment origin by barcode tagging. The methods include providing a plurality of solid support having clonal barcode templates or semi-clonal barcode templates immobilized thereon and providing a plurality of transpososomes, each transpososome comprising transposable DNA and transposase, wherein at least one transposable DNA in the transpososome is capable of ligating to the barcode template on the solid support directly or indirectly. A nucleic acid target contacts the transpososomes to form stable strand transfer complexes. The strand transfer complexes are captured to the solid support via non-specific binding. The barcode information on the solid support is attached to the nucleic acid target by ligation. The nucleic acid target is broken into fragments by breaking the strand transfer complexes, wherein at least one fragment is attached to a barcode template on the solid support. In some embodiments, the captured nucleic acid target with strand transfer complexes on the solid support is broken into fragments first by breaking the strand transfer complexes. The nucleic acid fragments are kept on the solid support by non-specific binding. The barcode information on the solid support is then attached to the nucleic acid fragments by ligation, wherein at least one fragment is attached to a barcode template on the solid support.

In one aspect, described herein are methods of tracking nucleic acid fragment origin by barcode tagging. The methods include providing a plurality of solid support having clonal barcode templates or semi-clonal barcode templates immobilized thereon and providing a plurality of transpososomes, each transpososome comprising transposable DNA and transposase, wherein at least one transposable DNA in the transpososome is capable of ligating to the barcode template on the solid support directly or indirectly. A nucleic acid target is captured to the solid support via non-specific binding. The transpososomes contact the non-specifically bound nucleic acid target to form stable strand transfer complexes on the solid support. The barcode information on the solid support is attached to the nucleic acid target by ligation. The nucleic acid target is broken into fragments by breaking the strand transfer complexes, wherein at least one fragment is attached to a barcode template on the solid support. In some embodiments, the captured nucleic acid target with strand transfer complexes on the solid support is broken into fragments first by breaking said strand transfer complexes. The nucleic acid fragments are kept on the solid support by non-specific binding. The barcode information on the solid support is then attached to the nucleic acid fragments by ligation, wherein at least one fragment is attached to a barcode template on the solid support.

In one aspect, described herein are methods for determining linkage information of a nucleic acid target. The methods comprise generating barcode tagged fragments of a nucleic acid target according to any one of methods described in this invention, determining the sequence of the nucleic acid fragments and the barcodes, and determining the linkage information of the nucleic acid target based on the barcode sequences when at least two fragments from the same nucleic acid target receiving identical barcode information.

In one aspect, described herein are methods for generating a soluble library of barcode tagged fragments of a nucleic acid target. In some embodiments, the soluble library comprises sequence information for a whole genome. In some embodiments, the soluble library comprises sequence information for a targeted region. In some embodiments, the soluble library is used for sequencing to determine phasing information of the nucleic acid target. In some embodiments, the soluble library is used for sequencing to determine the identity of duplicated reads.

In one aspect, described herein is a method for sequencing error correction of barcode design with degenerate bases at some or all positions without prior knowledge of the specific barcode sequence.

Figure 1:
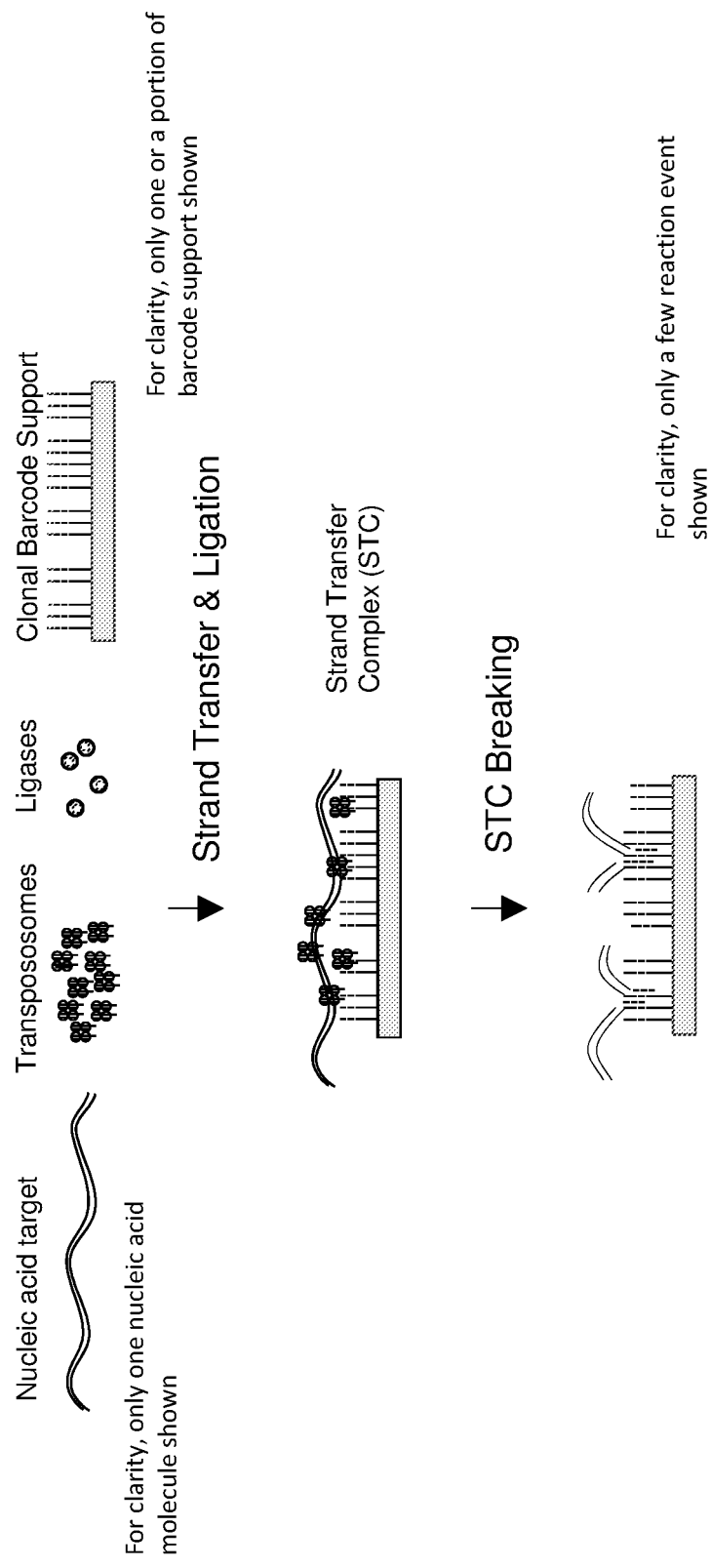
FIG. 1 illustrates a method of generating clonal barcode tagged nucleic acid fragments with simultaneous strand transfer and ligation reaction onto barcodedsolid support in an open bulk reaction without partition of nucleic acid target.

Transposases in all the figures are illustrated as a tetramer in the transpososome based on the MuA transposition system. However, other transposases can bealso used.

DETAILED DESCRIPTION

As used herein and in the appended claims, a barcode template and a solid support with clonal barcode templates or semi-clonal barcode templates immobilized thereon, i.e. barcoded solid support, are described in patent application WO2017/151828, which is hereby incorporated by reference in its entirety. In some embodiments, all the solid support has barcode templates attached. In some embodiments, only a fraction of solid support has barcode templates attached. The fraction of solid support with barcodes can be ranged from 1% to 99%. When a solid support is physically separable, such as a bead or a microparticle, barcoded solid support can be prepared by a clonal amplification method with or without enriching amplified solid support from unamplified solid support.

The term "adaptor" as used herein refers to a nucleic acid sequence that can comprise a primer binding sequence, a barcode, a linker sequence, a sequence complementary to a linker sequence, a capture sequence, a sequence complementary to a capture sequence, a restriction site, an affinity moiety, unique molecular identifier, and a combination thereof.

The term "transposase" as used herein refers to a protein that is a component of a functional nucleic acid protein complex capable of transposition and which is mediating transposition, including but not limited to Tn, Mu, Ty, and Tc transposases. The term "transposase" also refers to integrases from retrotransposons or of retroviral origin. It also refers to wild type protein, mutant protein and fusion protein with tag, such as, GST tag, His-tag, etc. and a combination thereof.

The term "transposon", as used herein, refers to a nucleic acid segment that is recognized by a transposase or an integrase and is an essential component of a functional nucleic acid-protein complex capable of transposition. Together with transposase they form a transpososome and perform a transposition reaction. It refers to both wild type and mutant transposon.

A "transposable DNA" as used herein refers to a nucleic acid segment that contains at least one transposon unit. It can also comprise an affinity moiety, un-natural nucleotides and other modifications. The sequences besides the transposon sequence in the transposable DNA can contain adaptor sequences.

The term "transpososome" as used herein refers to a stable nucleic acid and protein complex formed by a transposase non-covalently bound to a transposon. It can comprise multimeric units of the same or different monomeric unit.

A "transposition reaction" as used herein refers to a reaction where a transposon inserts into a target nucleic acid. Primary components in a transposition reaction are a transposon, a transposase or an integrase, and its target nucleic acid.

A "strand transfer reaction" as used herein refers to a reaction between a nucleic acid and a transpososome, in which stable strand transfer complexes form.

The term "strand transfer complex (STC)" as used herein refers to a nucleic acid-protein complex of transpososome and its target nucleic acid into which transposons insert, wherein the 3' ends of transposon joining strand are covalently connected to the two strands of its target nucleic acid. It is a very stable form of nucleic acid and protein complex and resists extreme heat and high salt in vitro (Burton and Baker, 2003).

A "transposase binding region" as used herein refers to the nucleotide sequences that are always within the transposon end sequence where a transposase specifically binds when mediating transposition. The transposase binding region may comprise more than one site for binding transposase subunits.

A "transposon joining strand" as used herein means the strand of a double stranded transposon DNA that is joined by the transposase to the target nucleic acid at the insertion site.

A "transposon complementary strand" as used herein means the complementary strand of the transposon joining strand in the double stranded transposon DNA.

A "solid support" as used herein is selected from the group consisting of a bead, a microparticle, a well, a tube, a slide, a plate, a flow cell, and a combination thereof, and wherein when the solid support is physically separable, such as a bead or a microparticle, the barcode template is clonally or semi-clonally immobilized onto the entire surface, and when the solid support is a contiguous flat surface, such as a well, a tube, a slide, a plate or flow cell, the barcode template is immobilized onto the surface as separable clonal clusters or semi-clonal clusters.

A "ligase" as used herein is selected from the group consisting of DNA ligase, or
RNA ligase in a wildtype, a mutant or a tagged version thereof, and a combination thereof; it is used for a ligation reaction.

A "capture reaction" as used herein means specific capture via ligation, hybridization, affinity binding with an affinity moiety, such as, biotin and streptavidin, antibody and antigen, click chemistry, or a combination of any of these, etc.

A "reaction vessel" as used herein means a substance with a contiguous open
space to hold liquid; it is selected from the group consisting
a tube, a well, a plate, a well in a multi-well plate, a slide, a spot on a slide, a droplet, a tubing, a channel, a bottle, a chamber and a flow-cell.

The methods and materials in this invention are exemplified by employing in vitro MuA transposition (Haapa et al, 1999 and Savilahti et al, 1995). Other transposition systems or combination of these different transposition systems can be used, e.g. Ty1 (Devine and Boeke, 1994), Tn7 (Craig, 1996), Tn10 and IS10 (Kleckner et al, 1996), Mariner transposase (Lampe et al, 1996), Tc1 (Vos et al, 1996), Tn5 (Park et al, 1992), P element (Kaufman and Rio, 1992) and Tn3 (Ichikawa and Ohtsubo, 1990), bacterial insertion sequences (Ohtsubo and Sekine, 1996), retroviruses (Varmus and Brown, 1989), and retrotransposon of yeast (Boeke, 1989).

The present invention relates in general methods and compositions for nucleic acid sequencing. In particular, the methods and compositions provided herein related in preparation of nucleic acid library and generation of sequencing data therefrom.

In one aspect, the methods and compositions relate to haplotype phasing the target nucleic acid. In some embodiments, the nucleic acid target is DNA. In some embodiments, the nucleic acid target is genomic DNA. In some embodiments, the nucleic acid target is amplified DNA. In some embodiments, the DNA is modified DNA. The modifications include un-natural nucleotide, affinity moiety, chemical treatment (e.g. bisulfite treated or formalin fixed paraffin embedded), and protein attachment (e.g. histone, transcription factor). In some embodiments, the nucleic acid target is synthesized DNA. In some embodiments, the nucleic acid target is RNA. In some embodiments, the nucleic acid target is mRNA. In some embodiments, the nucleic acid target is complementary DNA (cDNA). In some embodiments, the target nucleic acid is from single cell. In some embodiments, the target nucleic acid is cell free DNA. The length of the nucleic acid target can be varied a lot. It can range from about 50 bp to 1 Mb, or more. The longer the length of the nucleic acid targets, the better the result for phasing application. The number of nucleic acid targets in a reaction can be from one to billions, or even more. In some embodiments, a reaction vessel is a tube, a well, a plate, a well in a multi-well plate, a slide, a spot on a slide, a droplet, a tubing, a channel, a bottle, a chamber or a flow-cell. The reaction happens in a bulk format without partition of each nucleic acid target from another nucleic acid target within the total plurality of nucleic acid targets. Examples of such as partition are emulsion, wells, droplets, dilution, etc. The present invention dramatically simplifies the workflow and make it easy to scale and automate without the need of partition.

Strand Transfer Reaction onto Nucleic Acid Targets with Simultaneous Specific Capture of Barcode Template The present invention provides methods and compositions that capture nucleic acid targets by both strand transfer reaction with a transposition system and specific capture reaction, such as, with a ligase and/or hybridization, simultaneously to aclonally barcoded solid support. The captured nucleic acid target can be fragmented by breaking strand transfer complex, which generates small fragments from the nucleic acid target with a target-specific barcode attached (FIG. 1).

Figure 2:
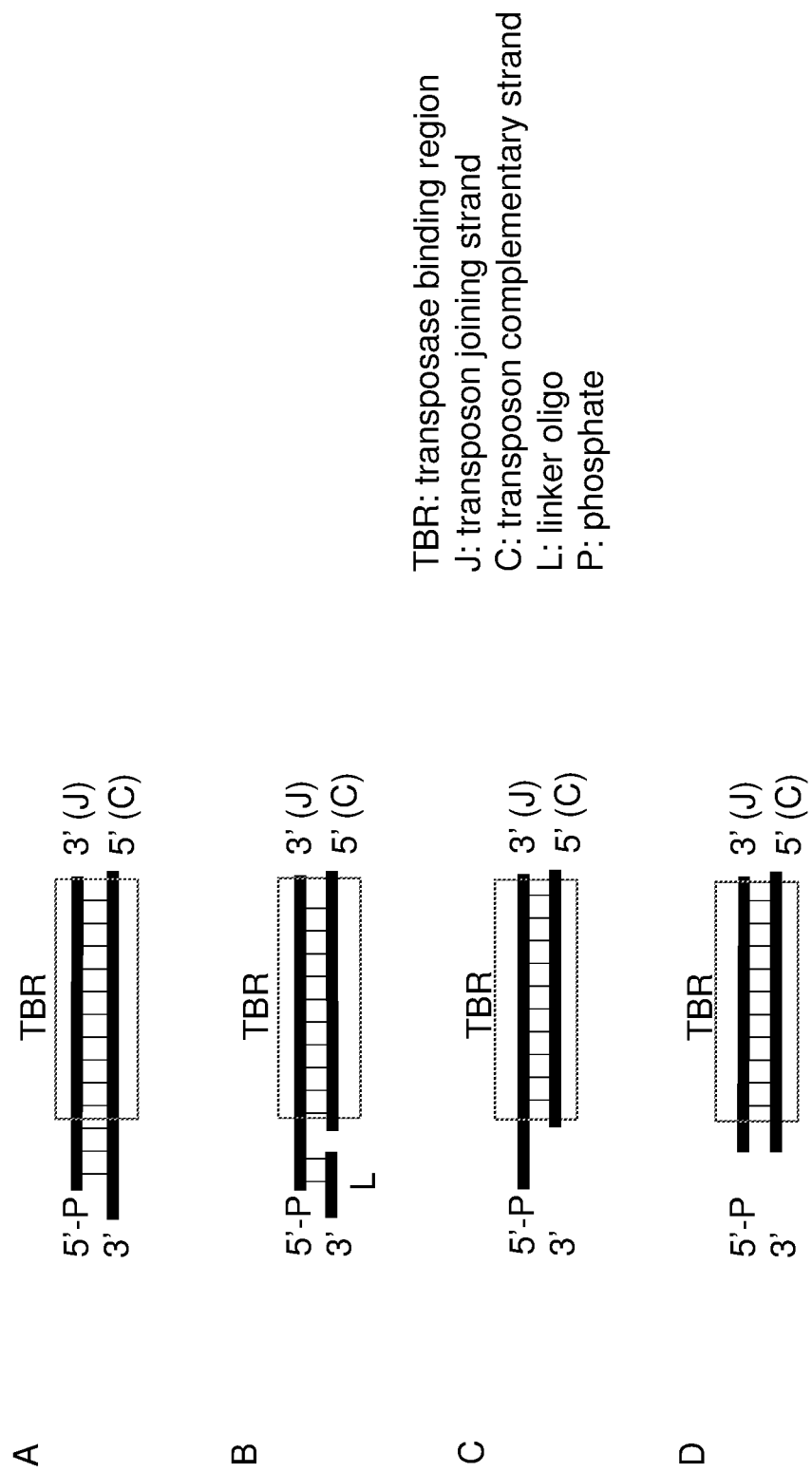
FIG. 2 shows different transposable DNA designs, (A) transposon complementary strand with 3' over hang in one piece, (B) transposon complementary strand with a separated complementary linker oligo, (C) transposon joining strand with a 5' overhang, (D) transposon with a blunt end at the non-joining end.

In one embodiment, a transposable DNA may comprise only one transposon sequence. The transposon sequence in the transposable DNA is thus not linked to another transposon sequence by a nucleotide sequence, i.e., the transposable DNA contains only one transposase binding region (FIG. 2). In addition, the 5' end of joining strand of the transposable DNA has a phosphate, which can ligate to a 3' end of any DNA strand with —OH group through single stranded end to end ligation, double stranded end to end ligation, or via a linker molecule. FIG. 2 shows some examples of ligatable transposable DNA. The 5' end of the transposon joining strand can ligate to the polynucleotide on the solid support with or without the presence of the transposases on the transposable DNA. In some cases, the 3' end of the transposon complementary strand and the 5' end of joining strand of the transposable DNA are in different length. In some cases, the 3' end of the transposon complementary strand and the 5' end of joining strand of the transposable DNA are in the same length. In some cases, the 3' end of the transposon complementary strand is modified with, such as, a dideoxy nucleotide, C3-spacer, a phosphate group, thiophosphate group, an azido group or amino linker to block self-ligation. In some cases, the 3' end of the transposon complementary strand may have a single nucleotide overhang or single nucleotide recess or mismatch nucleotide(s) to block self-ligation. In some cases, a single nucleotide overhang on both double stranded barcode template and a single nucleotide overhang double stranded transposon are complementary and used to facilitate ligation. In some cases, more than one nucleotide overhang on both double stranded barcode template and double stranded transposon may be used to facilitate ligation. In some cases, the barcode templates on the solid support are double stranded. In some cases, the barcode templates on the solid support are single stranded. In some cases, the barcode templates on the solid support are partially single stranded and partially double stranded. In some cases, some sequence variation in the transposon sequence is used as an additional sample identifier. In some cases, transposable DNA comprises an adaptor. In some cases, sequence variation in the adaptor is used as an additional sample identifier. Samples reacted with different transposons and/or transposable DNA sequences can be pooled together after the reaction to simplify downstream process when needed.

Figure 3:
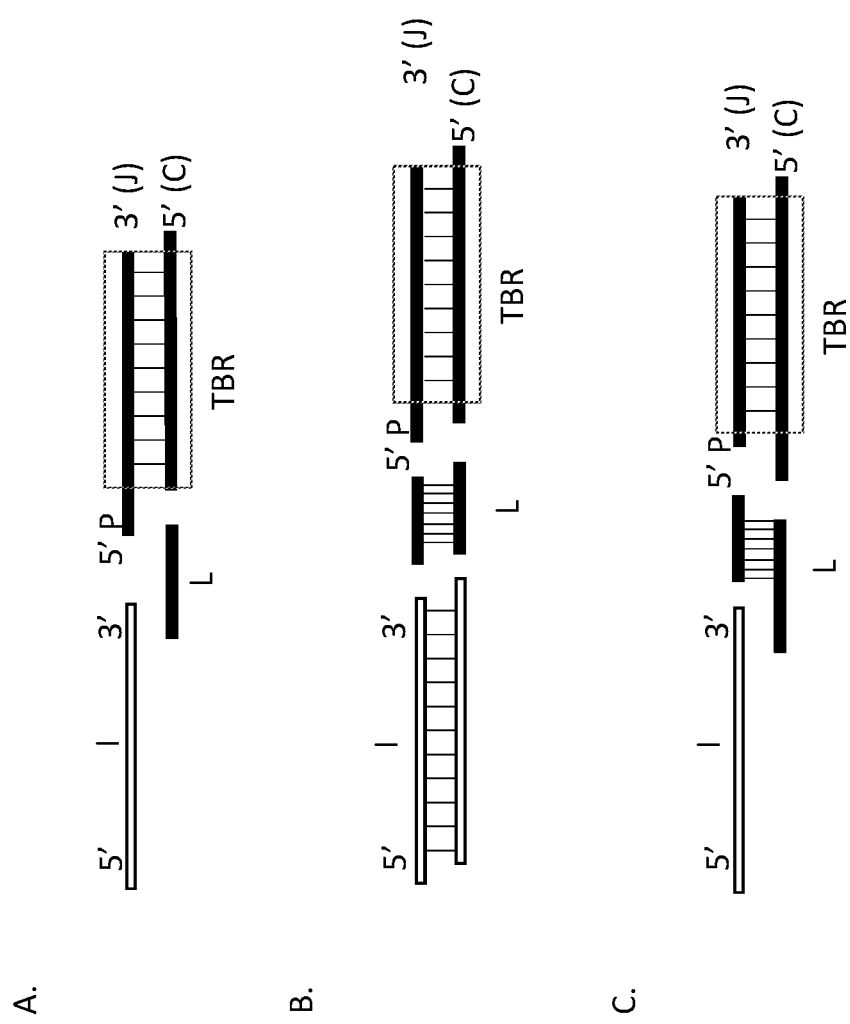
FIG. 3 shows examples of different free linker design. (A) single stranded linker, (B) double stranded linker, (C) partially double stranded linker.

In one embodiment, there are no complementary capture sequences between barcode templates on the solid support and transposable DNA which will be captured. A linker-based capture method may be used to facilitate the capture reaction. FIG. 3 shows some examples of linker-based ligation and/or capture. In one embodiment, the linker molecule is single stranded. In one embodiment, the linker molecule is double stranded. In one embodiment, the linker molecule is partially double stranded. In some cases, the linker oligonucleotides may be pre-bound with transposable DNA. In some cases, the linker oligonucleotides may be pre-bound with the immobilized polynucleotides on a solid support. In some cases, the linker oligonucleotides may be added only when capture reaction happens to join the 5' end of joining strand of the transposable DNA to 3' end of the immobilized polynucleotide on a solid support. The free linker method tends to generate fewer PCR by products than pre-bound linker method. The length of linker molecule can be varied, for example, 5 b(p), 10 b(p), 20 b(p), 30 b(p), 40 b(p), 50 b(p), 100 b(p), 200 b(p) or more.

A method for clonally fragmenting and barcoding nucleic acid targets is described as following (FIG. 1). In one reaction vessel, a double stranded nucleic acid target, an assembled transpososome, a ligase and a clonally or semi-clonally barcoded solid support are mixed together without compartmentation by emulsions or dilution. The transposable DNA in the transpososome is ligatable to the barcode template on the solid support. Strand transfer reaction between the transpososomes and the nucleic acid target, and ligation reaction between transposable DNA and barcode template happen simultaneously in the same solution. Stable STCs formed during strand transfer reaction will keep the nucleic acid target in one piece. The barcode sequence will be clonally attached to a nucleic acid target with STCs through ligatable transposable DNA in the STCs. After the reactions, the nucleic acid target is broken into small fragments by breaking STCs with a SOS solution. Many small fragments contain the barcode sequences and the fragments from the same nucleic acid target will have the same barcode. The simultaneous strand transfer reaction and barcode ligation reaction are critical for the high efficiency of this clonal barcode tagging method. The yield of barcode tagged fragments generated with present invention is much higher than that of method in the patent application WO2017/151828, wherein a nucleic acid target forms STCs with transpososomes in the solution first, transposable DNA in the STCs then ligate to a barcode template on a solid support. The reaction efficiency of present invention is also much better than the method in the U.S. Pat. No. 9,328,382B2 and the single tube article (Zhang et al, 2017), wherein the transpososomes are immobilized on a barcoded bead first, which then capture free nucleic acid targets in the solution by strand transfer reaction only. In the present invention, both ligation and strand transfer reactions are used to capture the nucleic acid targets. An explanation for low yield from method using ligation only for capture is that a nucleic acid target which is full of STCs may create steric hindrance which limits the ligation efficiency. An explanation for low efficiency from method using strand transfer only for capture is that transposable DNA are immobilized on the bead surface with fixed spatial arrangement and location, which may restrain the efficiency of transpososome formation and/or strand transfer reaction with the free nucleic acid targets. To fully take advantage of the simultaneous reactions of strand transfer and ligation, reaction conditions including buffer composition, pH and temperature are optimized.

A plurality of nucleic acid targets can be used in one reaction vessel. The reaction happens in a bulk format without partition of each nucleic acid target from another nucleic acid target within the total plurality of nucleic acid targets. The present invention dramatically simplifies the workflow and make it easy to scale and automate without the need of partition. The plurality of nucleic acid targets is dissolved in a solution homogeneously in order to be uniformly captured on a solid support after the reaction. In some embodiments, limiting the diffusion rate in the reaction solution is used to facility uniformity capture on the solid support. The solid support can be a continuous surface as in a well, a tube, a slide, a plate or a flow cell with isolated clonally or semi-clonally immobilized barcode template clusters. It can also be physically separated as individual bead or microparticle. The bead and microparticle can have sizes ranging from 50 nm to 100 μm, preferably 1 μm to 15 μm. Each bead or microparticle has a plurality of barcode templates with unique sequence. The major advantage in the present disclosure is that target specific barcode tagging can occur in an open bulk reaction without partition of nucleic acid targets with wells, microwells, spots, nanochannels, droplets, emulsion droplets, capsules, or dilution, etc. For better results, the bead or microparticle size should be controlled between 50 nm to 100 μm (diameter), preferably 1 μm to 15 μm, though it can be smaller than 50 nm or larger than 100 μm. For uniform reaction, beads or microparticles should keep suspended during reaction by controlling the viscosity of the solution using polyethylene glycol, pluronic, cellulose, agarose, or their derivatives, or other polymers, or a combination thereof, with a viscosity from 1 to 200 mPa·s at 20° c., most preferably from 1.5-30 mPa·s at 20° c. For the barcode clusters on a solid surface, such as a flow cell surface, the cluster size should be controlled between 50 nm to 200 μm (diameter), preferably 100 nm to 10 μm. The larger the cluster separation distance is, the smaller the chance of one target nucleic acid molecule being tagged by two or more barcodes.

Because the very stable nature of STC structure (Surette et al 1987, Mizuuchi et al 1992, Savilahti et al 1995, Burton and Baker 2003, Au et al 2004, Amini et al 2014) and clonal barcode template on a solid support, the barcode tagged fragments generated from this invention keep the identification of their origin nucleic acid target in the barcode sequence. Fragments from the same nucleic acid target share the same barcode sequence. This type of barcode tagged fragments is well known to be used for haplotype phasing, de nova assembly and other applications (Zheng et al, 2016, Zhang et al, 2017).

In one aspect, a nucleic acid target can be bound to a barcoded solid support non-specifically first. It then mixes with transpososome and ligase to attach the barcode information to the nucleic acid target covalently via simultaneous strand transfer reaction and ligation reaction.

Figure 4:
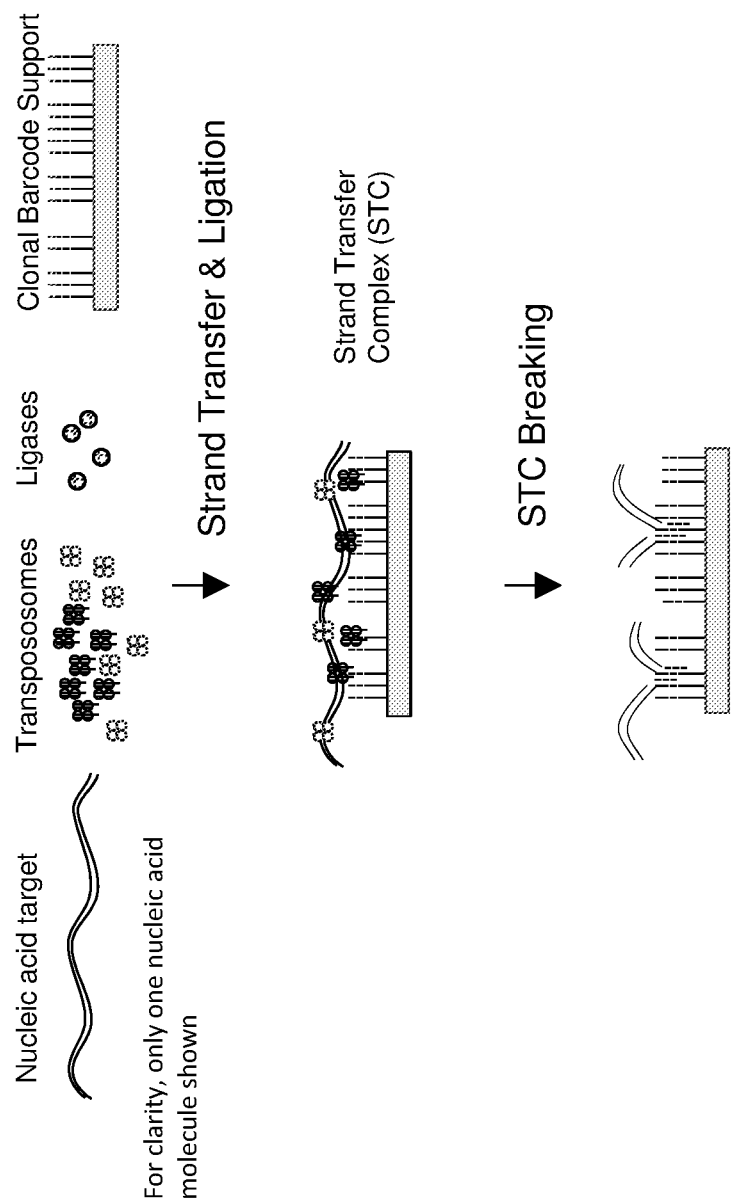
FIG. 4 illustrates a method of generating clonal barcode tagged nucleic acid fragments with simultaneous strand transfer and ligation reaction onto barcoded solid support using different transpososomes simultaneously in an open bulk reaction without partition of nucleic acid target.
Figure 5:
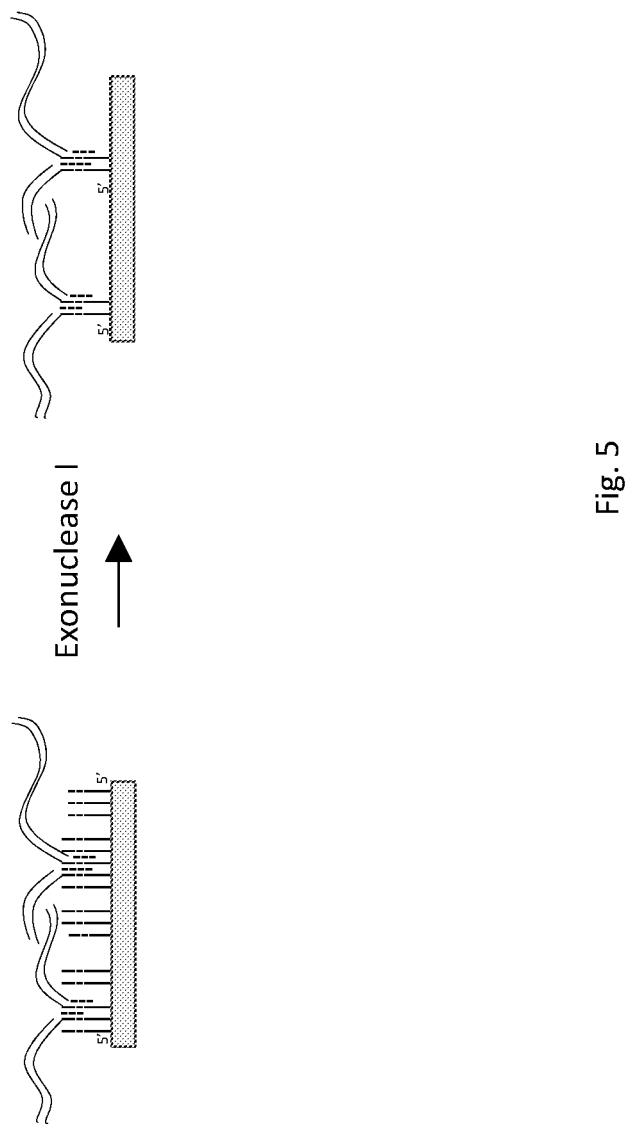
FIG. 5 shows removal of single stranded polynucleotides on the solid support
using exonuclease I.

In some embodiments, transpososomes are not pre-assembled before the reaction. A transposase and a transposable DNA are used directly in the reaction with a nucleic acid target, a ligase and a solid support. In some embodiments, the transposable DNA can be directly ligated to the barcode template on the solid support via single stranded ligation or double stranded ligation (FIG. 2). In some embodiments, a linker unit can be added in the simultaneous strand transfer and ligation reaction to facilitate ligation (FIG. 3). In some embodiments, all the transpososomes contain the same transposable DNA sequence. In some embodiments, the transpososomes contain different transposable DNA sequences (FIG. 4). In some embodiments, only one transposable DNA in the transpososomes can be ligated to barcode template (FIG. 4). In some embodiments, all transposable DNA in the transpososomes can be ligated to barcode template. In some embodiment, all the monomeric unit sequences of transposable DNA in the same transpososome are the same. In some embodiment, the monomeric unit sequences of transposable DNA in the same transpososome are different. In some embodiment, different transposases are used in the reaction. Different methods can be used to break strand transfer complex, such as, protease treatment, high temperature treatment, or a protein denaturing agent, e.g. SOS solution, guanidine hydrochloride, urea, etc., or a combination thereof. In some embodiments, a single stranded exonuclease may be used to remove unwanted single stranded polynucleotides on the solid support after the barcode tagging (FIG. 5).

Figure 6:
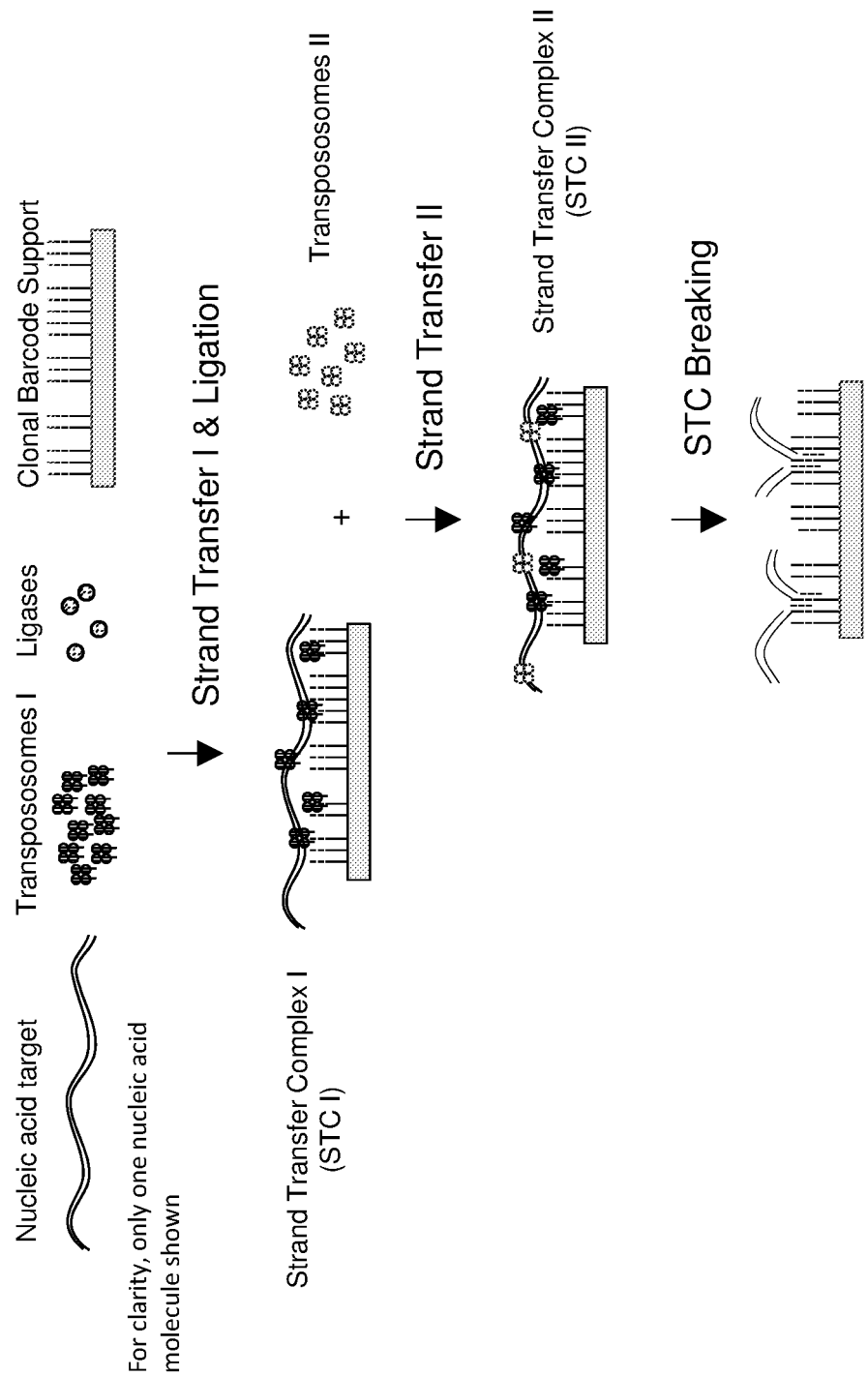
FIG. 6 illustrates a method of generating clonal barcode tagged nucleic acid fragments with simultaneous strand transfer and ligation reaction onto barcoded solid support using different transpososomes sequentially in an open bulk reaction without partition of nucleic acid target.
Figure 7:
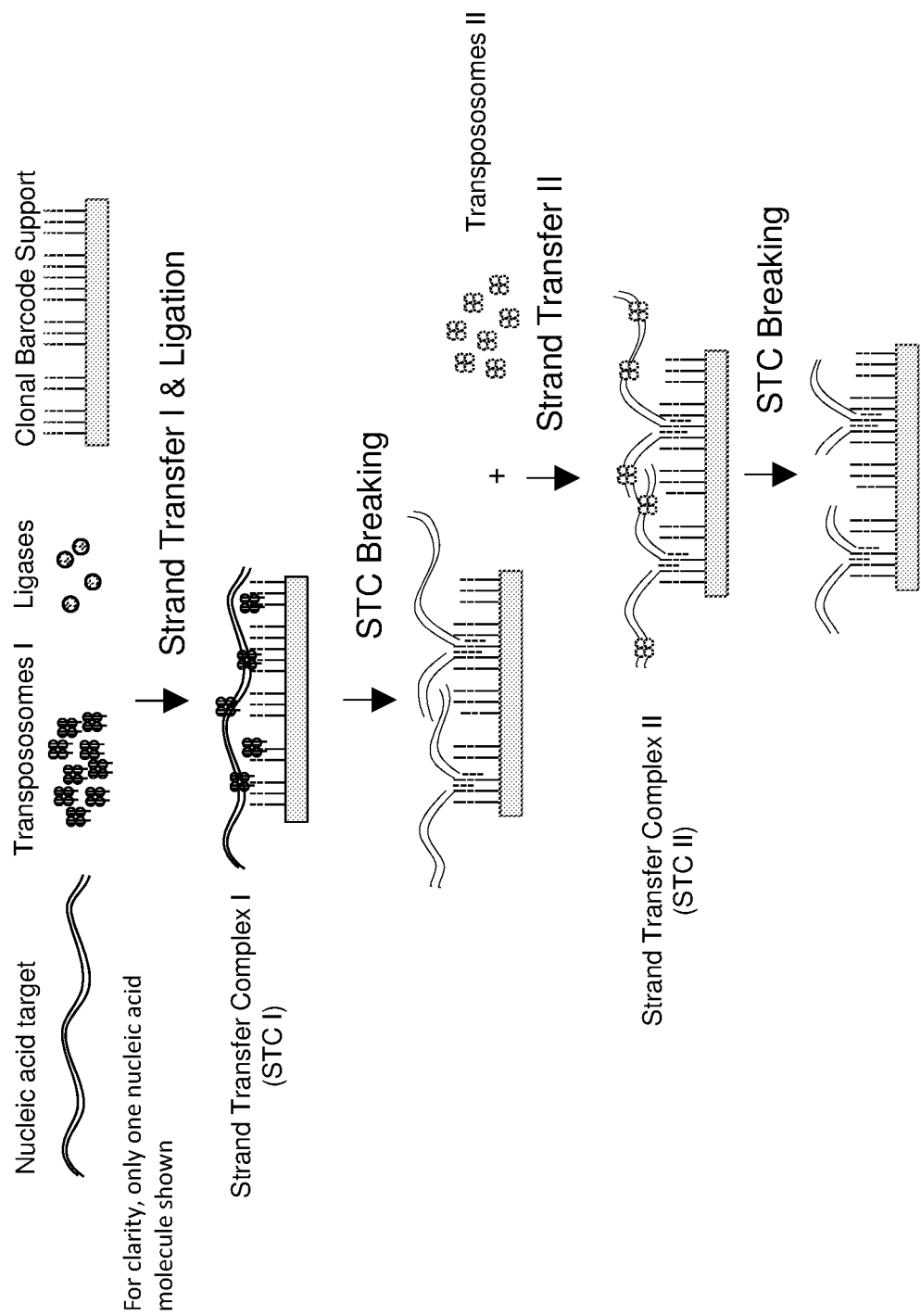
FIG. 7 illustrates a method of generating clonal barcode tagged nucleic acid fragments with simultaneous strand transfer and ligation reaction onto barcoded solid support using different transpososomes sequentially in an open bulk reaction without partition of nucleic acid target. The workflow order is different from that shown in FIG. 6.

In one aspect, transpososomes can be used sequentially in the reaction. In some embodiments, these transpsosomes are the same. In other embodiments, these transpososomes are different. In some embodiments (FIG. 6), a first transpososome mixes with a nucleic acid target, a ligase and a barcoded solid support to generate immobilized nucleic acid STC complex I on the solid support. A second transpososome is then added to attack the immobilized STC I and forms STC II. In some embodiments, the second transpososome may have a different type of transposon and transposase. In some embodiments, the transposable DNA in the second transpososome may have a different transposon sequence of the same type of transposon in the first transpososome. In some embodiments, the second transpososome may have a different transposable DNA sequence but with the same transposon sequence as the first transpososome. In some embodiments, the capture reactions, such as ligation and/or hybridization occur simultaneously again with the second strand transfer reaction. In some embodiment, a reaction buffer is optimized to be used for both first and second simultaneous strand transfer reaction with the transpososomes and capture reactionwith hybridization and/or ligation. Without the need of changing any reaction buffer among different steps can significantly simplify the workflow. Target specific barcode can be attached to the fragments after breaking the STCs. In some embodiments, the second transpososome may added only after breaking the first STCs (FIG. 7). The first and second transpososomes can be the same type or different type. This method has better strand transfer efficiency because steric hindrance effect from the first STCs is removed before the second strand transfer reaction. In some embodiments, the second strand transfer reaction is used to generate shorter fragment size. In some embodiments, the second transpososome is used to introduce a different adaptor or primer sequences from the first transpososome to facilitate downstream amplification and sequencing.

Figure 8:
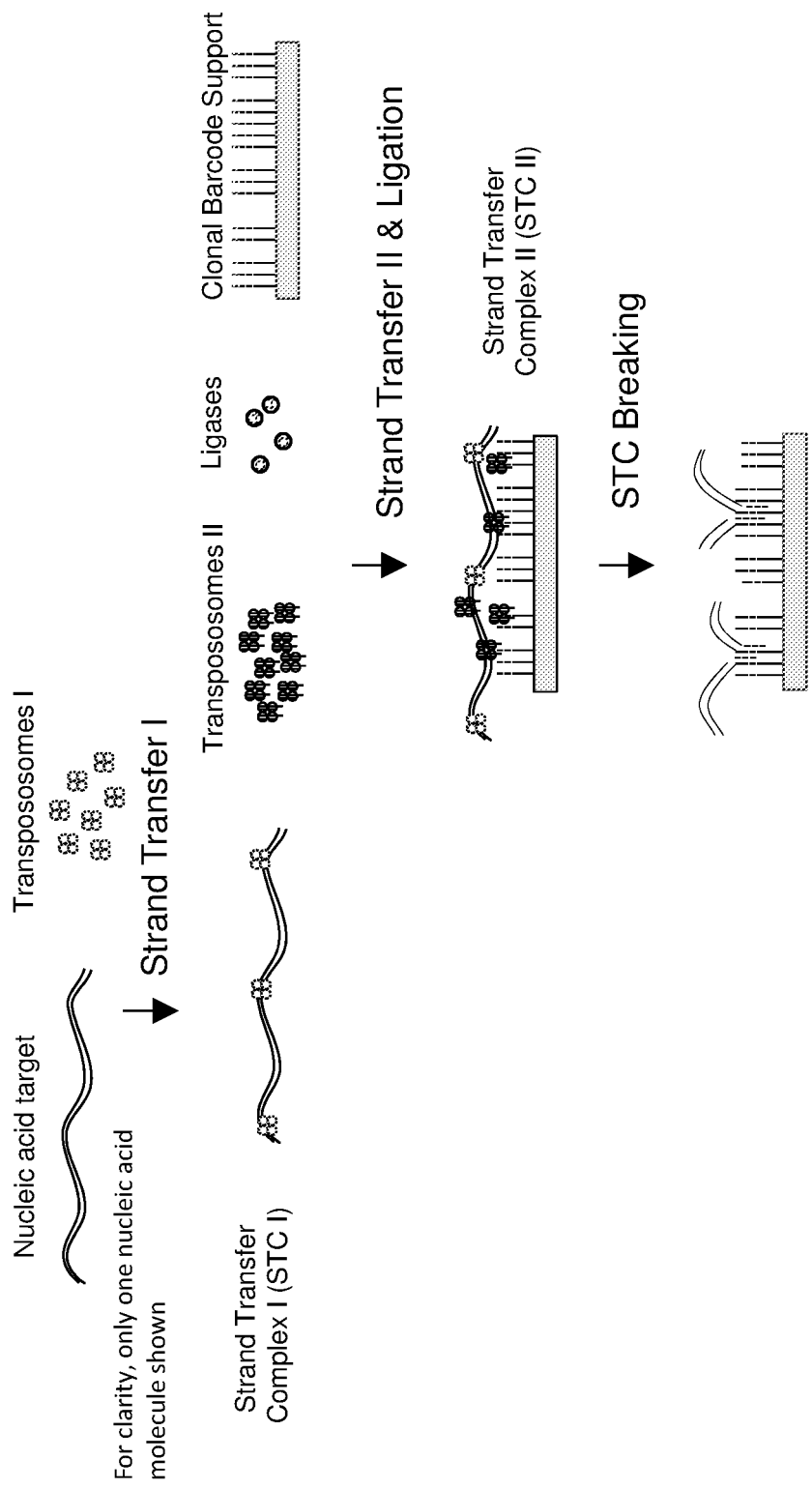
FIG. 8 illustrates a method with alternative workflow to generate clonal barcode
tagged nucleic acid fragments with simultaneous strand transfer and ligation reaction onto barcoded solid support.

In one aspect, a nucleic acid target is reacted with a first transpososome to form a stable STC I. The nucleic acid with STC I then react with a second transpososome, a ligase and a clonal barcoded solid support to generate target-specific barcode tagged fragments (FIG. 8).

Figure 9:
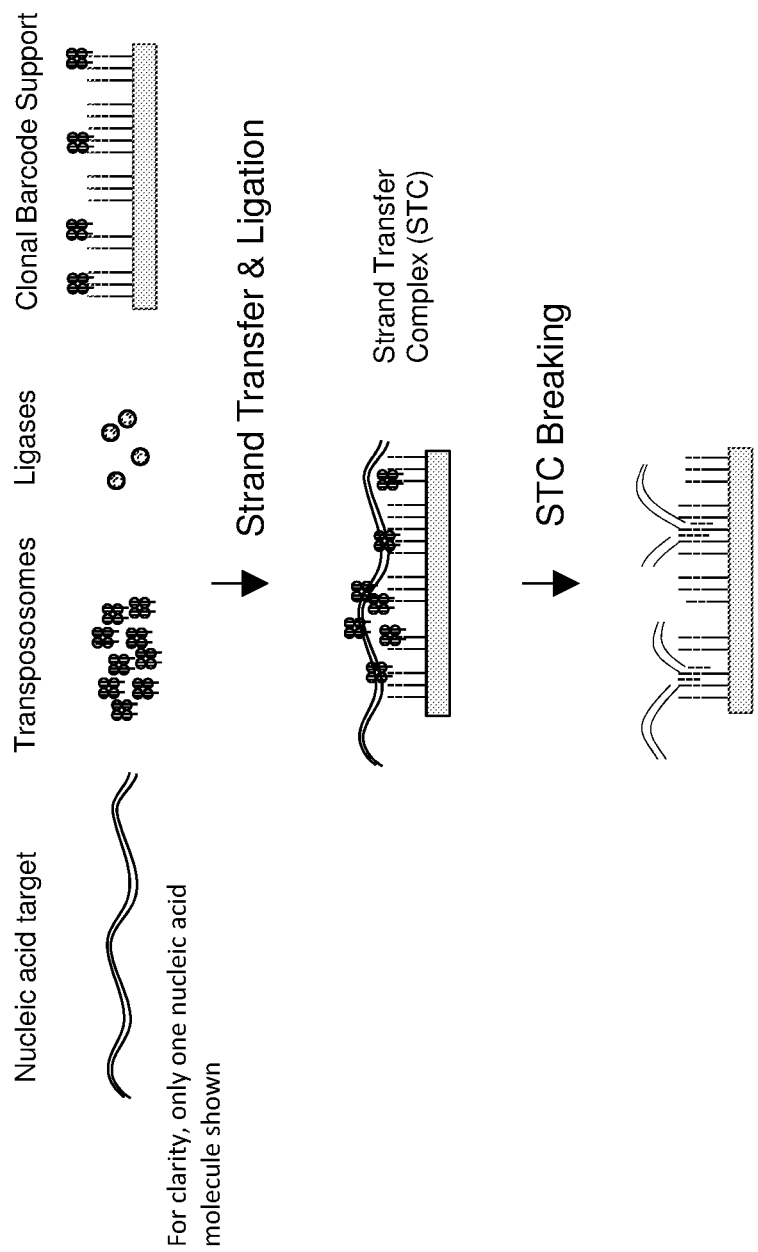
FIG. 9 illustrates a method with alternative workflow to generate clonal barcode tagged nucleic acid fragments with simultaneous strand transfer and ligation reaction onto barcoded solid support.

In one aspect, a transpososome can be attached to barcoded solid support first. To generate target specific barcode tagged fragments, a nucleic acid target, an in-solution transpososome, a ligase and the transpososome attached barcoded solid support are then mixed together in one reaction vessel as FIG. 9. In some embodiments, the in-solution transpososome is the same as the pre-attached transpososome on the solid support. In some embodiments, the in-solution transpososome is different from the pre-attached transpososome on the solid support.

In one aspect, a transposable DNA can be attached to barcode solid support first. To generate target specific barcode tagged fragments, a nucleic acid target, an in-solution transpososome, a ligase and the transposable DNA attached barcoded solid support are then mixed together in one reaction vessel. In some embodiments, the in-solution transpososome has the same transposon as the pre-attached transposable DNA on the solid support. In some embodiments, the in-solution transpososome has different transposon from the pre-attached transposable DNA on the solid support. In some embodiments, the in-solution transpososome is replaced with individual transposable DNA and transposase.

Figure 18:
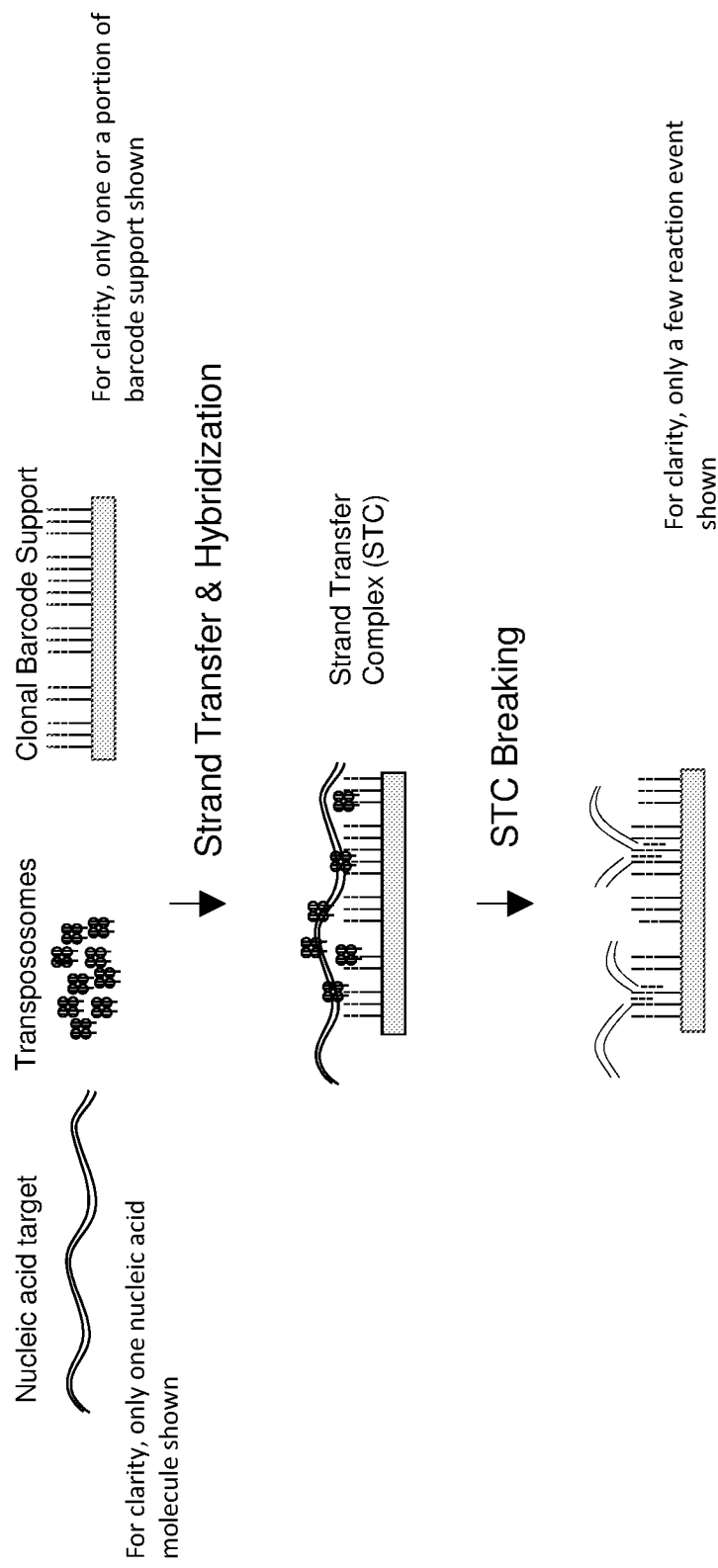
FIG. 18 illustrates a method of generating clonal barcode tagged nucleic acid fragments with simultaneous strand transfer and hybridization reaction ontobarcoded solid support in an open bulk reaction without partition of nucleic acid target.

In one aspect, the ligation reaction in the simultaneous strand transfer reaction and ligation reaction described in FIGS. 1, 4, 6, 7, 8 and 9, can be replaced with a hybridization reaction as FIG. 18. Ligase can be added later in the workflow, either before the STC breaking or after the STC breaking, to ligate hybridized transposable DNA covalently onto the barcoded template on the solid support.

In one aspect, the hybridization reaction in the simultaneous strand transfer reaction and hybridization reaction described in FIGS. 18, can be replaced with other capture reactions, such as, affinity tags (e.g. biotin and streptavidin), antibody to antigen, click chemistry, or a combination thereof.

Clonally Capture Nucleic Acid Target by Non-Specific Binding on a Solid Support for Barcode Tagging The present invention provides methods and compositions that capture nucleic acid targets by non-specific binding on a clonally barcoded solid support. The captured nucleic acid target can be covalently attached to the barcode templates on the solid support and generate small fragments from the nucleic acid target with a target-specific barcode attached.

Figure 10:
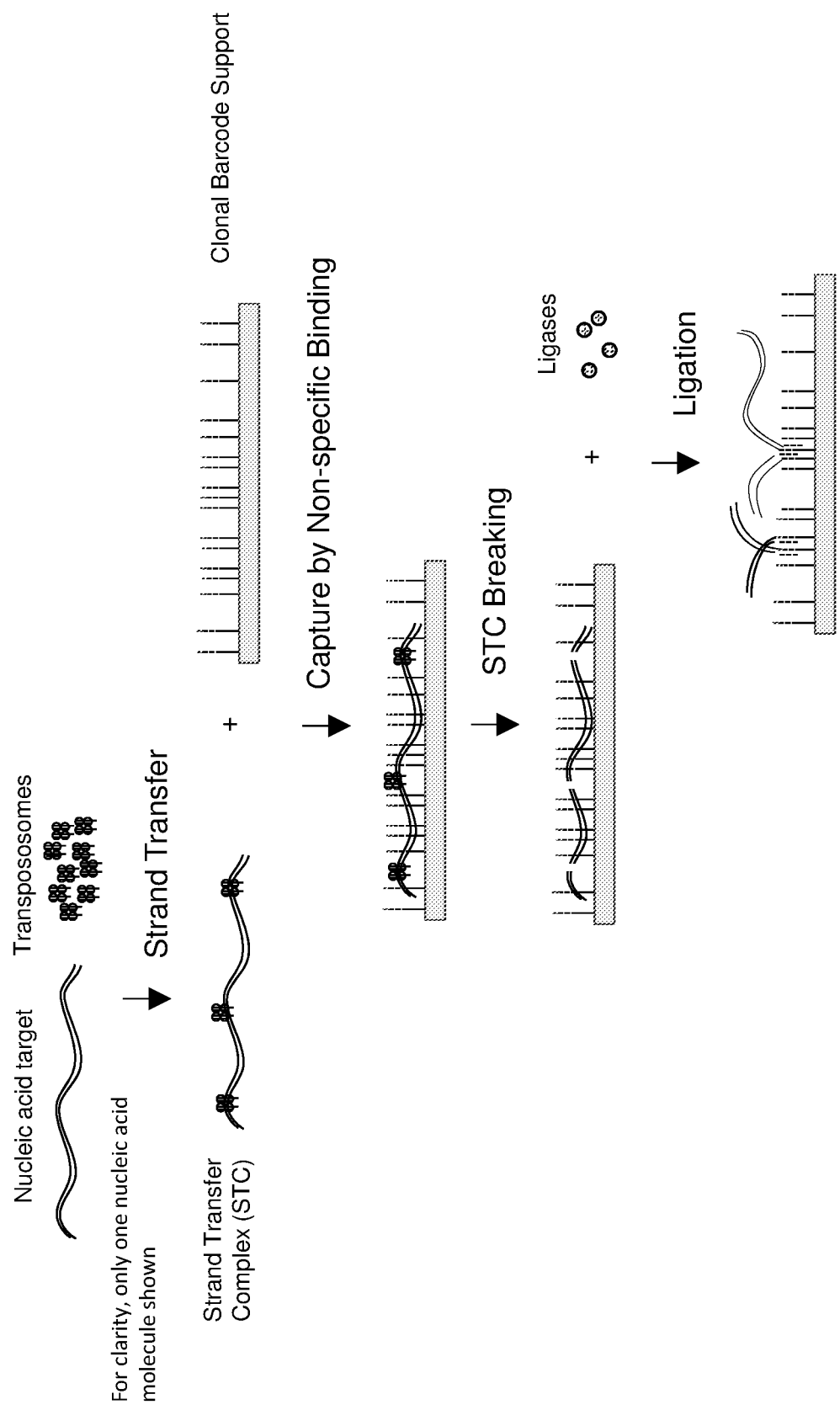
FIG. 10 illustrates a method of generating clonal barcode tagged nucleic acid fragments with non-specific binding and ligation onto barcoded solid support.
Figure 11:
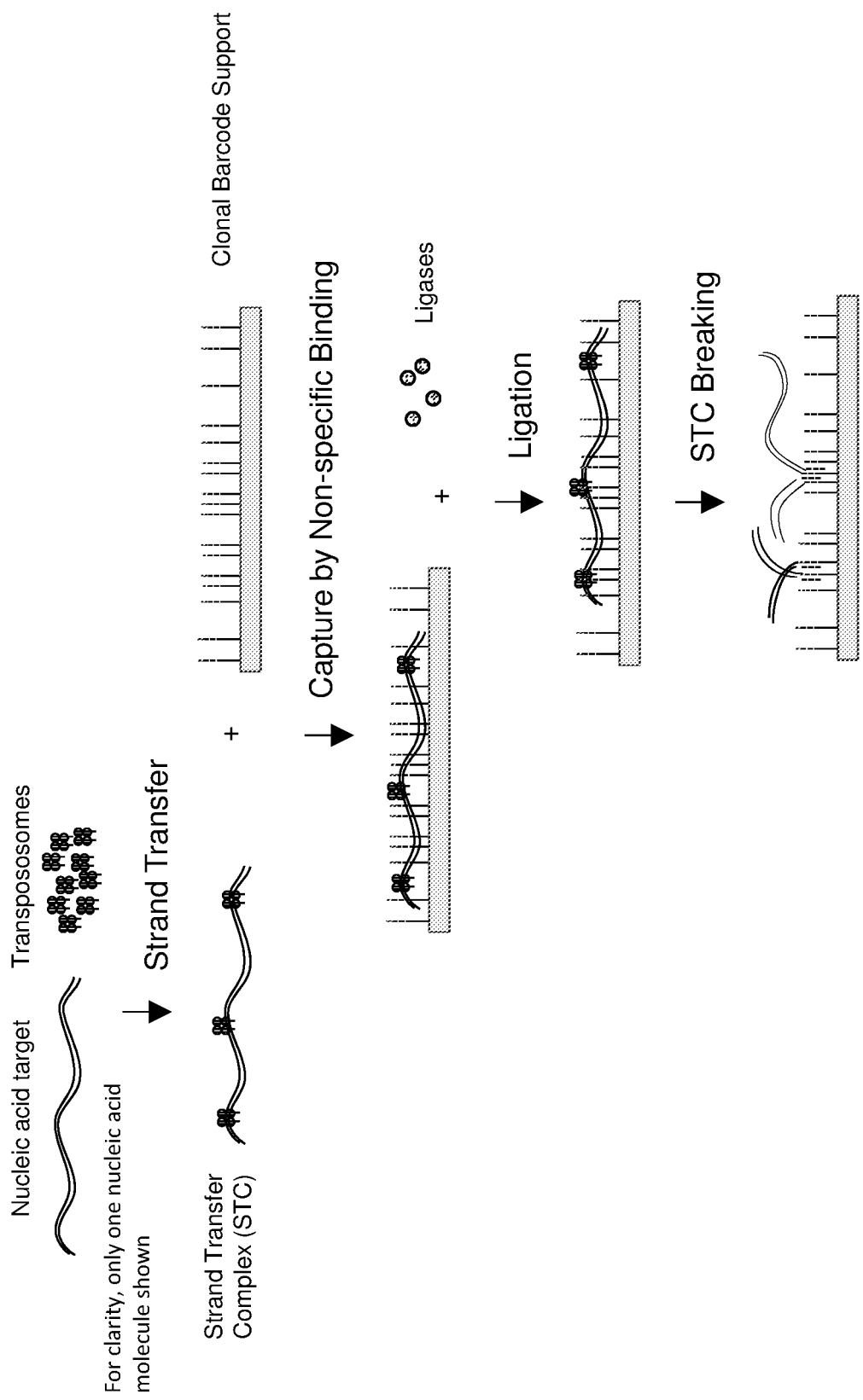
FIG. 11 illustrates a method with alternative workflow to generate clonal barcode tagged nucleic acid fragments with non-specific binding and ligation onto barcoded solid support.

In one aspect, a nucleic acid target reacts with transpososomes and forms strand transfer complexes. The nucleic acid target with the STCs bind non-specifically to a solid support with clonally or semi-clonally barcode templates immobilized on the surface (FIG. 10). In some embodiments, a nucleic acid target can bind non-specifically to a barcoded solid support first. The bound nucleic acid then reacts with transpososomes in the solution to form STCs on the solid support. In one aspect, the STCs are broken by a SOS treatment and the nucleic acid target breaks into small fragments which are still attached to the solid support by non-specific binding under the condition (FIG. 10). A ligase is added to covalently attach the small fragments to the barcode templates on the solid support, and generate small fragments attached with target specific barcode sequences (FIG. 10). In another aspect, the nucleic acid target with the STCs bound non-specifically on the solid support ligates to the barcode templates on the solid support via the ligatable transposable DNA in the STCs first. The STCs are then broken by a SOS treatment and generate small fragments attached with target specific barcode sequences (FIG. 11).

In one aspect, a nucleic acid target can bind non-specifically to a barcoded solid support first. The bound nucleic acid then reacts with transpososomes and ligase in the solution to form STCs and ligate the transposable DNA to the barcode templates simultaneously on the solid support.

Many conditions can make nucleic acid and nucleic acid & protein complex bind to a solid support non-specifically. Most notably, polyethylene glycol with salt (Lis and Scheif, 1975), polyamines and cobalthexamine (Pelta et al, 1996), and alcohols (Crouse and Amorese, 1987) are widely used to precipitate and/or condense nucleic acid.

In one aspect, the ligation reaction described in the invention, can be replaced with other capture reactions, such as, hybridization, affinity tags (e.g. biotin and streptavidin), antibody to antigen, click chemistry, or a combination thereof.

Figure 12:
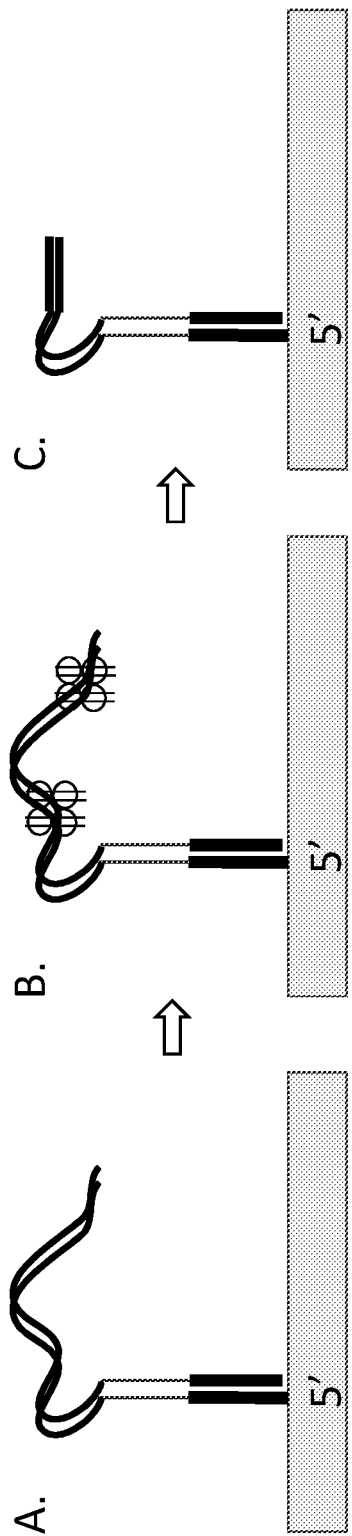
FIG. 12 shows a method of introducing adaptor onto immobilized barcode tagged fragments using transpososome.
Figure 13:
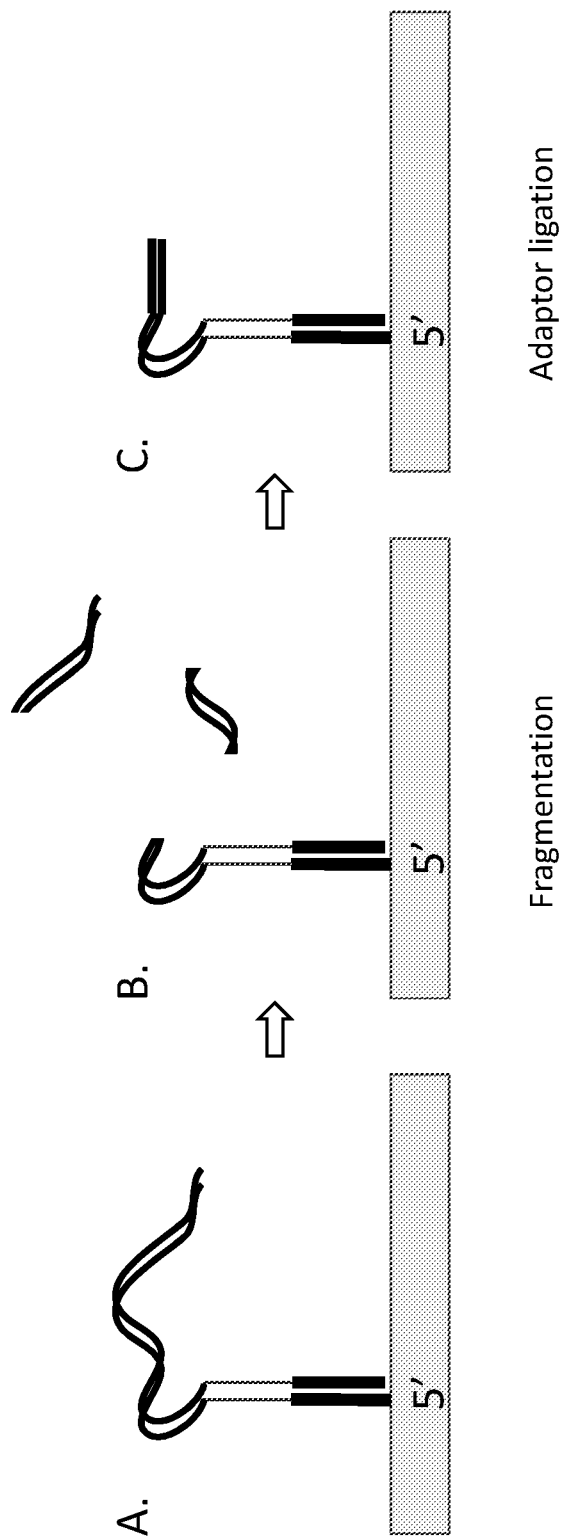
FIG. 13 shows a method of introducing adaptor onto immobilized barcode tagged fragments with fragmentation and ligation reaction.
Figure 14:
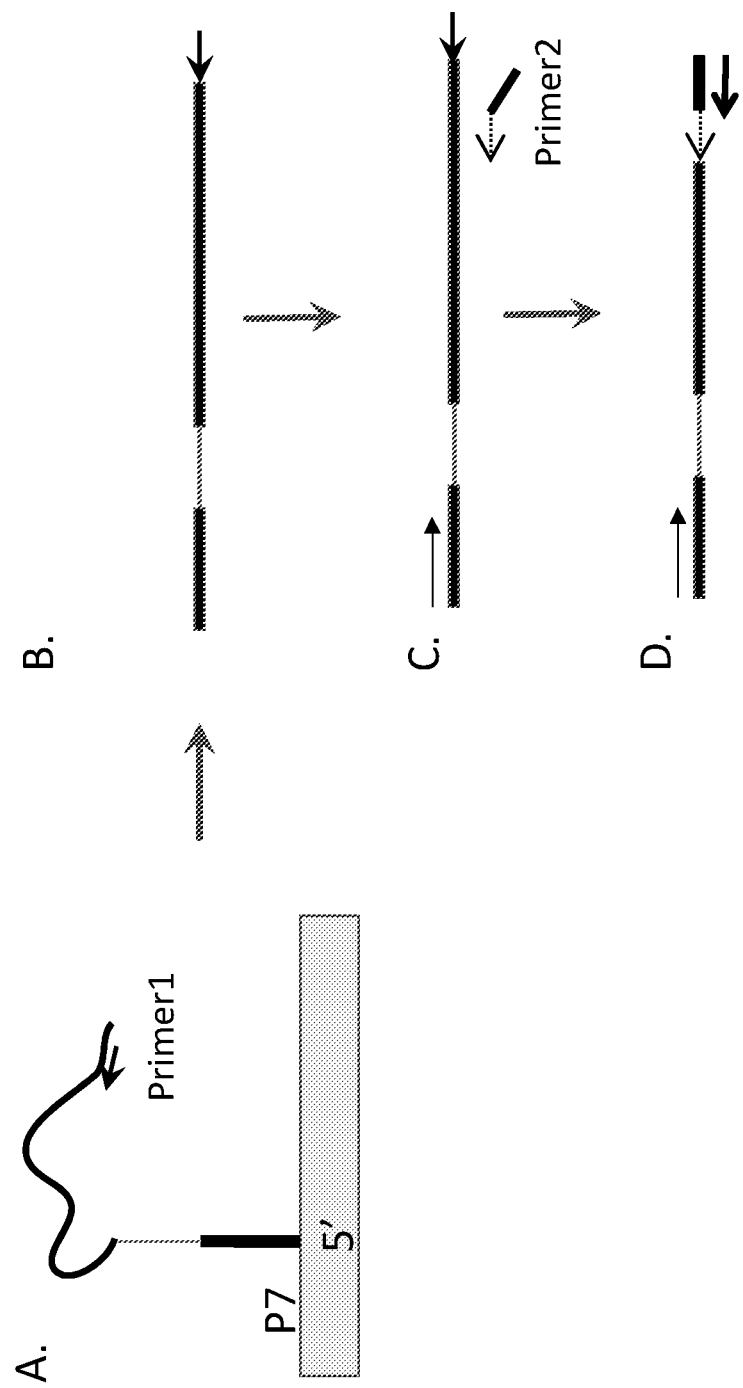
FIG. 14 shows a method of releasing a copy or copies of immobilized barcode tagged fragments by primer extension and/or PCR amplification.
Figure 15:
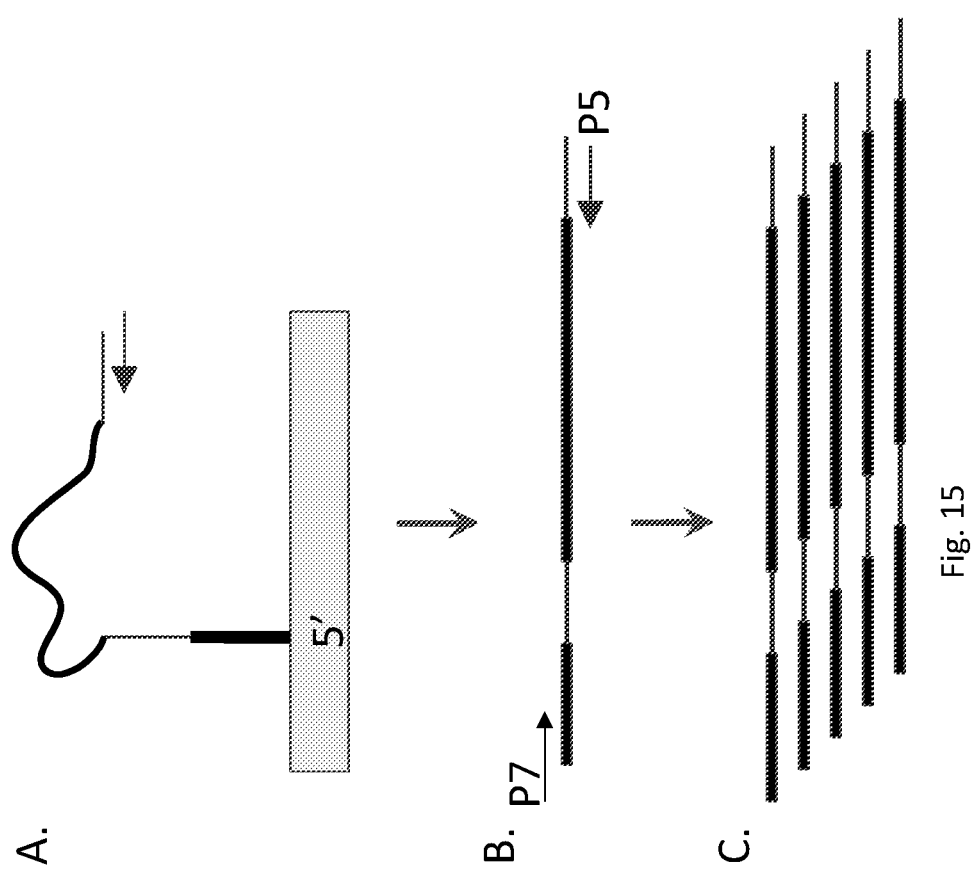
FIG. 15 is an example of Illumina's sequencing library generated from barcode tagged fragments.

Releasing Clonally Barcode Tagged Nucleic Acid Fragments to Generate Sequencing Library The barcode tagged fragments are immobilized on the solid support. They can be used to make sequencing library. In some embodiments, it can be further manipulated for other applications, such as, treatment with bisulfite for methylation study. In some embodiments, additional sequencing adaptor can be attached to the barcode tagged fragments using transposase-based tagging method (FIG. 12). In some embodiments, barcode tagged fragments can be further fragmented with physical shearing methods and/or enzymatic fragmentation methods, then additional sequencing adaptor can be ligated on (FIG. 13). Immobilized barcode tagged fragments can be released from the solid support in many ways. In one embodiment, a cleavable link or a rare restriction site may be included in the oligonucleotide sequence which is attached to the solid support. With a cleavage reaction or a restriction enzyme digestion, the barcode tagged fragments can be released from the solid support. In some cases, a primer extension may be performed to make a copy or copies of the barcode tagged fragments (FIG. 14A). In some embodiments, the primer is random primer. In some embodiments, the primer is target specific primer (FIG. 14A, 14C). The target of the specific primer can be exon, intron, gene, exome, etc. More detail application for targeted sequencing is described in patent application WO 2017/151828. Further PCR amplification with primers which are specific for a sequencing platform, e.g., PS and P7 primers for Illumina's SBS library (FIG. 15), or P1 and A primers for Ion Torrent's library, may generate sequencing ready libraries for the specific sequencing platform. When a library is being made by releasing the barcode tagged fragments from the solid support, a primer with sample specific index may be used. In some cases, the sequence in the barcode template may be used as sample specific index. The released barcode tagged fragments with sample specific index can mix with tagged fragments from other samples with their own sample specific index together for further downstream workflow in order to increase sample preparation throughput and simplify the process. The constructed libraries can be sequenced to determine sequences of both barcode and nucleic acid fragment, and determine the linkage information of the nucleic acid target based on the barcode sequences when at least two fragments from the same nucleic acid target received identical barcode information. The linkage information can be used for haplotype phasing, structural variation detection, CNV detection, etc. The barcode information can also be used to differentiate the sources of duplicated reads from amplification or from sequencing.

Assemble Barcode Sequencing Reads into Long Reads

This invention provides methods and compositions to clonally barcode tag nucleic acid samples in an open bulk reaction without sophisticated compartmentation or partition scheme as other methods. The barcode tagged fragments may be from a whole genome sample, or a portion of a genome, or a particular targeted region, or metagenomic samples. The sequencing reads generated from these barcode tagged fragments contain the barcode information which can be used to identify the original target of these fragments. These short sequencing reads with the same barcode can be grouped together and cluster along the original nucleic acid targets. Depending on which transposase system is used, among these reads with the same barcode, starting ends of two originally adjacent reads from the same nucleic acid target will share some bases of reverse complimentary sequences (5 bases for MuA transposase system and 9 bases for Tn5transposase system). These overlap sequences can further link the barcode reads together. In principle, it can re-construct the original nucleic acid target completely when all the tagged fragments are captured by barcoded solid support and sequenced. They provide useful long range linkage information to be used for haplotype phasing. The longer the original nucleic acid targets are, the longer the linkage information will be, the more useful they are for phasing application. An analysis pipeline which can be developed for full genome assembly or structural variation analysis using these barcode reads for both de nova sequencing and resequencing. In one case, all the sequencing reads may be used for standard shotgun assembly analysis to establish many initial contigs first. The barcode information can then be used to phase the initial contigs into much longer contigs. These barcode tagging methods can also be used for phasing the targeted gene, genes, or exome. These barcode tagging methods may also be used as a tool for differentiating the duplicated reads in the targeted sequencing application. This method improves sequencing assay detection limit on heterogeneous samples, e.g., somatic mutation detection in a cancer biopsy sample or circulating tumor cell/DNA.

A Sequencinig Error Correction Method for Barcode Design with Random Degenerate Bases Any sequencing technologies will generate sequencing errors. Most NGS sequencing technologies have 0.1%-1% raw read sequencing error rate. Forbarcode design using random degenerate bases, especially using all 4 possible degenerate bases, A, C, G, or T for a given position, it is very difficult to differentiate a sequencing error from a true base variant by design for the position.

The present invention provides a method enabling to detect and correct sequencing errors at the degenerate bases without a prior sequence reference for the positions. The total sequence diversity of a barcode population preferably is much larger than actual number of unique barcode sequences used in a given experiment. Sequencing read count should be at least greater than 2-fold of number of unique barcode used in the experiment. The deeper the sequencing depth, the better the error correction function.

For example, a random 10-mer barcode design with four degenerate bases A, C, G and T at all positions, NNNNNNNNNN, will have maximum 4^10=1,048,576 different unique barcode sequences in total. If 1,000 unique barcode sequences were randomly chosen from this barcode pool and used in a sequencing library construction, and sequencing generated 20,000 barcode reads. Most of the 1,000 unique barcode sequences should have more than 1 read with an average 20-read per barcode, and total 1,000 unique barcode sequences should be detected if there were no sequencing error. However, due to sequencing error, actual number of unique barcodes identified after sequencing will be more than 1,000. Because most of sequencing errors generated randomly, a barcode sequence which contains a sequencing error or errors will most likely become a new unique barcode sequence outside of the original 1,000 barcode sequences. And, a barcode with sequencing error(s) will also most likely be associated with one sequencing read only. In addition, due to the chance of generating multiple sequencing errors in a 10-mer sequence will be very low, the sequence of barcode with sequencing error(s) will most likely have 1 or 2-base different from its original correct barcode sequence. Such erroneous barcodes can be identified by comparing the sequence homology of a unique barcode which has only one sequencing read with those unique barcodes which have multiple sequencing reads. One expects to find a barcode with 1 base mismatch or 2-base mismatch in those unique barcodes with multiple sequencing reads, which is most likely the actual correct barcode sequence for the unique barcode with only one sequencing read if it is generated due to sequencing error during sequencing.

The degenerate bases in the barcode can be all 4, or any 3, or any 2 bases from A, C, G, and T (U). In the barcode design, some positions can be nondegenerate bases. Other feature may be used in the barcode design to limit the length of homopolymer. The error correction method described in the invention can still work for these barcode designs.

This barcode design with degenerate bases can not only be used for sequencing application with sequencing reads, but also be associated with other information and/or identities, such as, color, index, ID, cluster, location, container, or compartment information. In some embodiments, it can be used for DNA or RNA. In some embodiments, it can be used for protein, antibody, and chemical, etc.

Although the invention has been explained with respect to an embodiment, it isto be understood that many other possible modifications and variations can be made without departing from the spirit and scope of the invention as herein described.

Further, in general with regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Moreover, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

Lastly, all defined terms used in the application are intended to be given their broadest reasonable constructions consistent with the definitions provided herein. All undefined terms used in the claims are intended to be given their broadest reasonable constructions consistent with their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

Example 1

Figure 16:
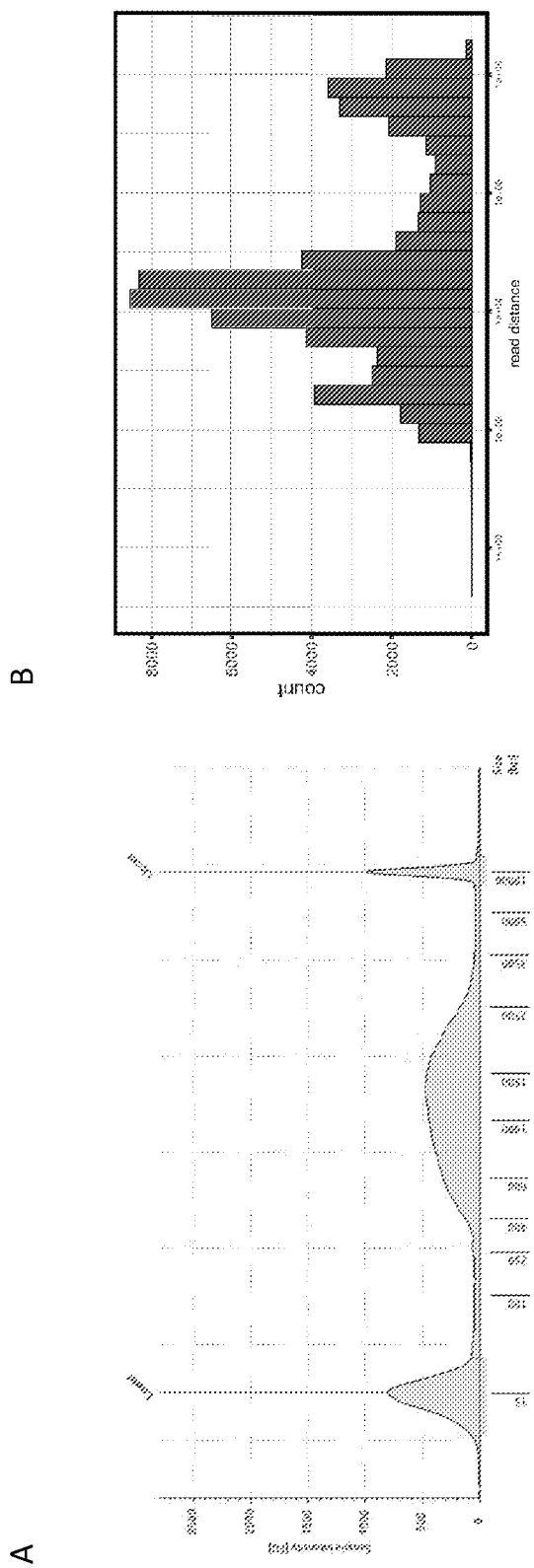
FIG. 16 shows an electropherogram of a barcode tagged Illumina sequencing library ran on a TapeStation (A) and sequencing read count histogram based on read distance to the next alignment for reads with the same barcode (B).

This example describes a method of target specific barcode tagging of genomic DNA with simultaneous strand transfer and ligation onto barcoded beads in an open bulk reaction without partition of genomic DNA (FIG. 4). Clonally barcode beads were prepared as described in patent application WO 2017/151828. Each barcode sequence was 18-base in length. All the beads including those without clonally amplified barcode templates were collected directly after BEAMing reaction (Diehl et al, 2005). Two MuA transpososomes were pre-assembled with two different MuA transposable DNA separately. The MuA transposable DNA in one MuA transpososome had a ligatable 5' end transposon joining strand and could hybridize and/or ligate to the barcode template on the barcoded beads. Double stranded barcode templates on the beads were denatured into single stranded. 20 million denatured beads were incubated with 5 ng genomic DNA extracted from human embryonic kidney cells 293FT, the two preassembled MuA transpososomes and T4 DNA ligase in a reaction buffer which enabled both strand transfer reaction and ligation reaction at substantially the same time at 37° C. for 30 minutes. Reaction was terminated with 0.5% SOS solution. Washed beads were treated with exonuclease I to remove single stranded polynucleotides, and then used for 15-cycle PCR amplification to release immobilized barcode tagged DNA fragments. PCR products were purified with 0.8× AMPure XP beads to remove small primer dimers and PCR by-products, and examined using a high sensitivity D5000 screentape on a TapeStation (FIG. 16A). The purified PCR products were sequenced on an Illumina MiniSeq instrument. Reads with the same barcode sequence were sorted for each barcode based on the reference genome alignment location. Read distance to the next alignment was calculated and read count frequency along the read distance was plotted in FIG. 16B. When barcoded reads kept the linkage information of reads from tagged DNA fragments, piling up of proximal reads was expected. The read distance from the original DNA fragment before tagging would also pile up as distal reads with much longer distance. A bi-modal distribution of read count frequency plot would be expected, which was exactly observed in the FIG. 16B. Although the sequencing depth was very limited in a multi-sample MiniSeq run, strong enrichment of shorter distance proximal reads demonstrated successful barcode reads contiguity.

Example 2

Figure 17:
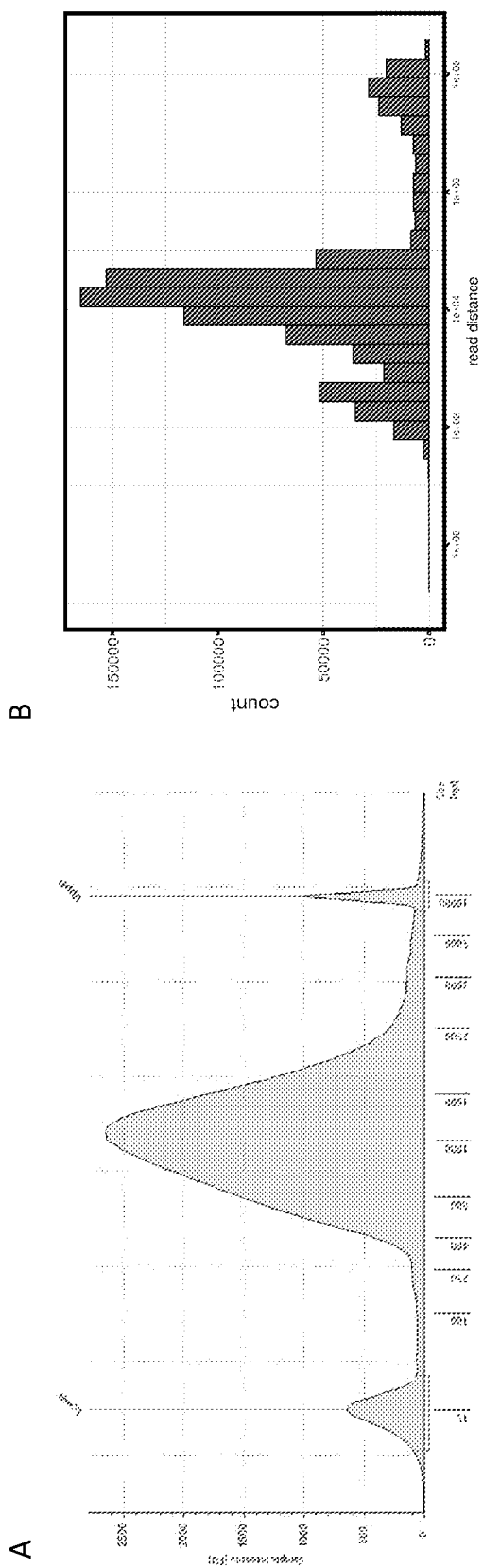
FIG. 17 shows another electropherogram of a barcode tagged Illumina sequencing library ran on a TapeStation (A) and sequencing read count histogram based on read distance to the next alignment for reads with the same barcode(B).

This example describes a method of target specific barcode tagging of genomic DNA with simultaneous strand transfer and ligation onto barcoded beads in an open bulk reaction without partition of genomic DNA (FIG. 7). One MuA transpososome comprised a MuA transposable DNA which had a ligatable 5' end transposon joining strand and could ligate to the barcode template on the barcoded beads. 20 million barcoded beads were incubated with 5 ng genomic DNA extracted from human embryonic kidney cells 293FT, the ligatable MuA transpososomes and T4 DNA ligase in the reaction buffer at 37° C. for 30 minutes. Reaction was terminated with 0.5% SOS solution. Washed beads were then reacted with another MuA transpososome and exonuclease I. The reaction was stopped with 0.5% SOS again. The beads with barcode tagged fragments were used for 15-cycle PCR amplification to release immobilized barcode tagged fragments. This method generated fewer PCR by products than the method in the Example 1. PCR products were purified with 0.8× AMPure XP beads to remove small primer dimers and PCR by-products, and examined using a high sensitivity D5000 screentape on a TapeStation (FIG. 17A). The purified PCR products were sequenced on an Illumina MiniSeq instrument. Reads with the same barcode sequence were sorted for each barcode based on the reference genome alignment location. Read distance to the next alignment was calculated and read count frequency along the read distance was plotted in FIG. 17B. When barcoded reads kept the linkage information of reads from tagged DNA fragments, piling up of proximal reads was expected. The read distance from the original DNA fragment before tagging would also pile up as distal reads with much longer distance. A bi-modal distribution of read count frequency plot would be expected, which was exactly observed in the FIG. 17B. Although the sequencing depth was very limited in a multi-sample MiniSeq run, strong enrichment of shorter distance proximal reads demonstrated successful barcode reads contiguity.

Example 3

10 ng genomic DNA from HapMap sample NA12878 was used to generate barcode tagged Illumina sequencing library with the method illustrated in FIG. 4. 2×75 bp paired end sequencing were performed on Illumina NextSeq system. Over 600 million paired end reads were pooled for haplotype phasing analysis using a HapCUT2 algorithm (Edge P et al, 2017). There were approximately 22-fold genome coverage depth after removing duplicated reads. The largest phased block size was 9.5 Mb and N50 phased block size was 1.7 Mb with a switch error rate at 0.14%.

Example 4

An 18-base barcode design with 14 degenerate bases was used to generate clonal barcode templated beads. A barcode tagged sequencing library from 0.5 ng *E. coli* DH1 OB genomic DNA sample with lambda DNA mixed in was prepared using the method illustrated in FIG. 7 with these barcode templated beads. This library was pooled with other libraries and sequenced on an Illumina MiniSeq system with following sequencing cycle condition: read 1 (71-cycle), index 1 (18-cycle), index 2 (8-cycle) and read 2 (71-cycle). Sequencing error correction algorithm was developed based on this invention and applied to these sequencing data. This algorithm first sorted out unique barcodes and their associated tagged reads. It then compared unique barcodes that had only a single tagged read (single-read barcodes), with unique barcodes that had 2 or more tagged reads (multi-read barcodes) for mismatches only by one base. When there was only one such multi-read barcode identified, its sequence would be considered as the original sequence of the unique barcode with single associated tagged read, i.e. the correct sequence of this barcode so that a barcode error correction would be performed.

An example result is shown in Table 1, below.

TABLE 1

| Barcode Error Correction Statistics | |
|---|---|
| Read Mapped | 94.16% |
| Unique Barcode Count | 550,271 |
| Unique Barcode with Single Taqqed Read | 211,484 |
| Error Corrected Barcode Count | 110,140 |
| Unique Barcode with Multiple Tagged Reads | 338,787 |
| Tagged Read Count of Unique Barcode with Multiple Tagged Reads | 4,728,347 |

Among total 550,271 barcodes with unique sequence identified during the sequencing run, there are 211,484 barcodes associated with only one tagged read. Error correction was performed for these unique barcodes with single tagged read. 110,140 of them were able to identify only one 1-base different barcode counterpart from the 338,787 unique barcodes with multiple tagged reads. These barcode sequences are corrected accordingly.

These data were further used for de nova assembly analysis using a modified assembler based on SPAdes (Bankevich A et al, 2012). A top-level summary of de nova assembly results is in the Table 2, below. With further optimization on the assembler, we expect better assembly results will be achieved.

TABLE 2 de nova AssemblIV Stalts" t"ICS

| | |
|---|---|
| # contigs (>= 1000 bp) | 4 |
| # contigs (>= 50000 bp) | 1 |
| Total length (>= 1000 bp) | 4,579,504 |
| Total length (>= 50000 bp) | 4,532,858 |
| Reference Length | 4,686,137 |
| NG50 | 4,532,858 |
| # misassemblies | 3 |
| Genome fraction (%) | 96.4 |
| Duplication ratio | 1.003 |
| NGA50 | 3,197,999 |
| NGA75 | 1,065,699 |
| LGA50 | 1 |
| LGA75 | 2 |

Example 5

Figure 19:
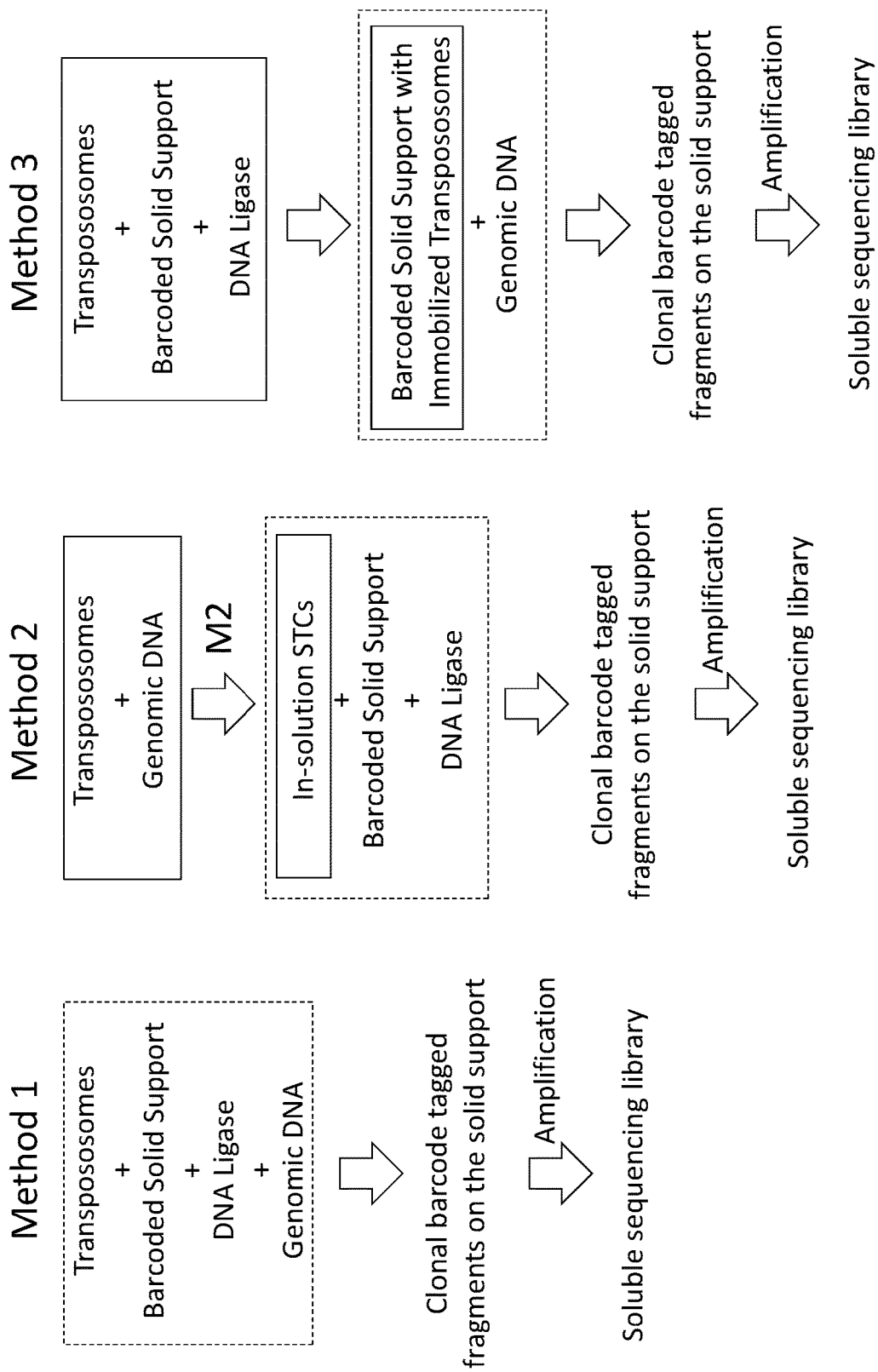
FIG. 19 shows three different transposase-based methods to generateclonal barcode tagged fragments for sequencing library construction.

We compared three different transposase-based methods to generate clonal barcode tagged fragments for sequencing library construction (FIG. 19). Method 1 was the simultaneous strand transfer and capture reactions disclosed in this invention. 1 ng E. coli genomic DNA was mixed with ligatable transpsosomes, DNA ligase and 20 million beads among which there were 1 million clonally barcode templated beads in the same reaction buffer to generate clonal barcode tagged fragments and soluble sequencing library by further PCR amplification. Method 2 and 3 were two methods using separate strand transfer and capture reactions to generate clonal barcode tagged fragments.

Figure 20:
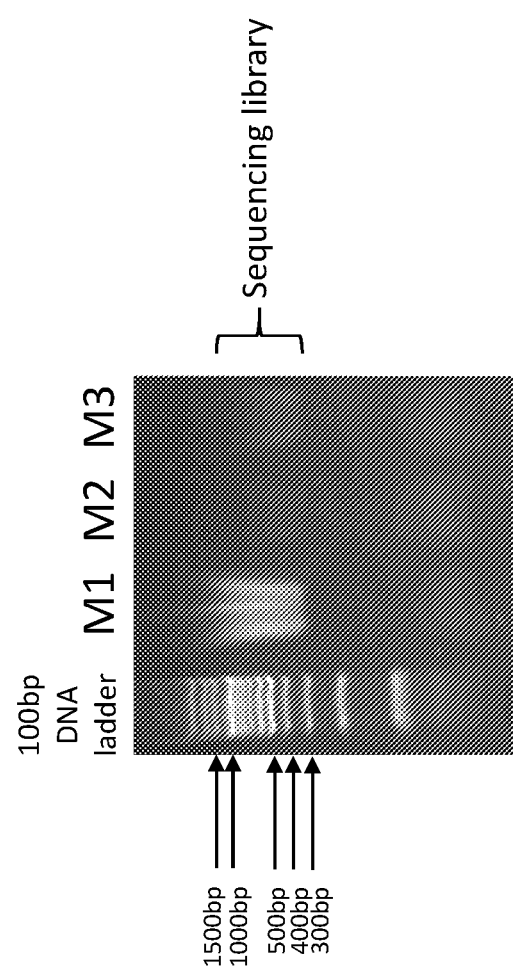
FIG. 20 shows a 2% agarose E-gel EX picture of three amplified sequencing libraries using three different transposase-based methods. Ml, Method 1; M2, Method 2; M3, Method 3. The fragment sizes of the 100 bp DNA ladder from top to bottom are 3000 bp, 2000 bp, 1500 bp, 1000 bp, 900 bp, 800 bp, 700 bp, 600 bp, 500 bp, 400 bp, 300 bp, 200 bp, and 100 bp, respectively.

Method 2 was to generate in-solution STCs first by mixing ligatable transpsosomes with 10 ng E. coli genomic DNA; $\frac{1}{10}^{th}$ of these in-solution STCs which contained 1 ng original E. coli genomic DNA was then mixed with DNA ligase and 20 million beads among which there were 1 million clonally barcode templated beads in a ligation buffer to capture the in-solution STC onto the beads. Method 3 was to immobilize the ligatable transpososomes onto the barcode templated beads first by mixing transpsosomes and DNA ligase with 20 million beads among which there were 1 million clonally barcode templated beads in a ligation buffer; the reacted beads were washed to remove ligase and then reacted with 1 ng E. coli genomic DNA in a strand transfer reaction buffer. At last the same number of beads from these three methods were used for PCR amplification to generate soluble sequencing libraries by the same number of PCR cycles. The PCR products were loaded onto a 2% agarose E-gel EX to compare their yield (FIG. 20). Method 1 (FIG. 20, lane M1) produced the most library product as we expected, which demonstrated the superior performance of Method 1 to the other two methods (FIG. 20, lane M2 and lane M3).

REFERENCES

Amini S. et al. 2014. Nature Genetics, 46(12): 1343-1349.
Au T et al. 2004. EMBO J., 23: 3408-3420.
Bankevich A. et al. 2012. J Comput Biol. 5: 455-77.
Boeke J. D. 1989. Transposable elements in *Saccharomyces cerevisiae* in Mobile DNA. pp. 335-374 in Mobile DNA, edited by D. E. BERG and. M. M. HOWE.
Burton B. M. and Baker T. A. 2003. Chemistry & Biology 10: 463-472.
Chen Z. et al. 2017. Foreign Patent Application WO 2017/151828 A1.
Craig N. L. 1996. Transposon Tn7. Curr. Top. Microbial. Immunol. 204: 27-48.
Crouse J. and Amorese D. 1987. Focus, 7(4): 1-2.
Devine S. E. and Boeke, J. D. 1994. Nucleic Acids Research, 22(18): 3765-3772.
Diehl F. et al. 2005. PNAS, 102 (45): 16368-16373.
Drmanac R., Peters B. A. and Alexeev A. 2016. U.S. Pat. No. 9,328,382 B2.
Edge P., Bafna V. and Bansal V. 2017. Genome Res., 27(5): 801-812.
Haapa S. et al. 1999. Nucleic Acids Research, 27(13): 2777-2784.
Ichikawa H. and Ohtsubo E. 1990. J. Biol. Chem., 265(31): 18829-32.
Kaufman P. and Rio D. C. 1992. Cell, 69(1): 27-39.
Kleckner N. et al. 1996. Curr. Top. Microbial. Immunol., 204: 49-82.
Mizuuchi M., Baker T. A. and Mizuuchi K. 1992. Cell, 70, 303-311.
Lampe D. J., Churchill M. E. A. and Robertson H. M. 1996. EMBO J., 15(19): 5470-5479.
Lis J. T. and Schleif R. 1975. Nucleic Acid Research, 2(3): 383-389.
Ohtsubo E. and Sekine Y. 1996. Curr. Top. Microbial. Immunol., 204:126.
Park B. T., Jeong M. H. and Kim B. H. 1992. Taehan Misaengmul Hakhoechi, 27(4): 381-9.
Pelta J., Livolant F. and Sikorav J. L. 1996. J. Biological Chemistry, 271: 5656-5662.
Savilahti H., Rice P. A., and MiZuuchi K. 1995. EMBO J., 14: 4893-4903.
Surette M., Buch S. J. and Chaconas G. 1987. Cell, 70: 303-311.
Varmus H. and Brown. P. A. 1989. Retroviruses, in Mobile DNA. Berg D. E. and Howe M. eds. American Society for Microbiology, Washington D. C. pp. 53-108.
Vos J. C., Baere I. and Plasterk R. H. A. 1996. Genes Dev., 10(6): 755-61.
Zhang F. et al. 2017. Nature Biotechnology, 35(9): 852-857.
Zheng G. X. et al. 2016. Nature Biotechnology, 34(3): 303-311.

What is claimed:

1. A method for tracking nucleic acid fragment origin by barcode tagging comprising:
   a. providing a plurality of solid supports having clonal barcode templates or semi-clonal barcode templates immobilized thereon;
   b. providing a plurality of transpososomes, each transpososome comprising transposable DNA and transposase, wherein at least one transposable DNA in the transpososome is capable of being captured by said barcode template on said solid support directly or indirectly;
   c. providing a nucleic acid target;
   d. wherein steps a, b, and c occur in one reaction vessel concurrently to attach a barcode information on said solid support to said nucleic acid target by simultaneous strand transfer and capture reactions without additional partition of each nucleic acid target from another nucleic acid target within the total plurality of nucleic acid targets;
e. breaking said nucleic acid target into fragments by breaking strand transfer complexes, wherein at least one fragment is attached to the barcode template on the solid support.

2. The method of claim 1, wherein said solid support is selected from the group consisting of a bead, a microparticle, a well, a tube, a slide, a plate, a flow cell, and a combination thereof, and wherein when the solid support is physically separable, such as a bead or a microparticle, the barcode template is clonally or semi-clonally immobilized onto the entire surface, and when the solid support is a contiguous flat surface, the barcode template is immobilized onto the surface as separable clonal clusters or semi-clonal clusters.

3. The method of claim 1, wherein the clonal barcode templates or semi-clonal barcode templates immobilized on said solid support are produced by methods of direct synthesis, clonal amplification, or a combination thereof.

4. The method of claim 3, wherein said clonal amplification is selected from the group consisting of emulsion PCR, bridge PCR, isothermal amplification, template walking, nanoball generation, and a combination thereof.

5. The method of claim 1, wherein the said barcoded solid support is prepared by a clonal amplification method without separating amplified and unamplified populations.

6. The method of claim 1, wherein the said barcoded solid support is prepared by a clonal amplification method with only or predominantly enriched amplified populations.

7. The method of claim 2, wherein said bead and microparticle have sizes ranging from 50 nm to 100 μm.

8. The method of claim 1, wherein said reactions are in a buffer system with a controlled viscosity to decrease diffusion and increase suspension by adding a substance selected from the group consisting of polyethylene glycol, pluronic, cellulose, agarose, and their derivatives, and other polymers, and a combination thereof.

9. The method of claim 8, wherein the buffer system at working concentration has a viscosity of about 1-200 mPa·s at 20° c.

10. The method of claim 1, wherein the transpososomes are individual transposable DNAs and transposases, wherein the individual transposable DNAs and transposases are not pre-assembled into transpososome complexes.

11. The method of claim 1, further comprising adding a second transpososome after step d.

12. The method of claim 1, further comprising adding a second transpososome after step e.

13. The method of claim 1, wherein said nucleic acid target is pre-attached to said solid support by non-specific binding.

14. The method of claim 1, wherein said capture reaction in the reaction vessel is by ligation, or by hybridization, or by affinity tag, or by antibody and antigen reaction, or by click chemistry, or a combination thereof.

15. The method of claim 1, wherein said capture reaction comprises first hybridization and then ligation.

16. The method of the claim 1, wherein said barcoded solid support has transposable DNAs or transpososomes pre-attached to the end of some barcode templates immobilized on the solid support.

17. The method of claim 1, wherein said transposase is selected from the group consisting of Tn, Mu, Ty, and Tc transposases in a wildtype, a mutant or a tagged version thereof, and a combination thereof.

18. The method of claim 1, wherein the transposase is a MuA transposase, or a Tn5 transposase in a wildtype or a mutant or a tagged version thereof, or a combination thereof.

19. The method of claim 1, wherein said transposable DNA contains a transposon, wherein the transposon is selected from the group consisting of Tn, Mu, Ty, and Tc transposon DNAs in a wildtype or a mutant version thereof, and a combination thereof.

20. The method of claim 19, wherein said transposon is a MuA transposon, or a Tn5 transposon, wild type or mutant, or a combination thereof.

21. The method of claim 1, wherein said transposable DNA further comprises an adaptor sequence.

22. The method of claim 1, wherein said transposable DNA capable of being captured by said barcode template has no complementary sequences to said barcode template, and the capture of said transposable DNA to said barcode template is facilitated by a linker.

23. The method of claim 1, wherein said transpososome comprises at least one type of transposase, at least one type of transposable DNA or a combination thereof.

24. A method for tracking nucleic acid fragment origin by barcode tagging comprising:
a. providing a plurality of solid supports having clonal barcode templates or semi-clonal barcode templates immobilized thereon;
b. providing a plurality of transpososomes, each transpososome comprising transposable DNA and transposase, wherein at least one transposable DNA in the transpososome is capable of being captured to said barcode template on said solid support directly or indirectly;
c. contacting a nucleic acid target with said transpososomes to form stable strand transfer complexes;
d. attaching said strand transfer complexes to said solid support via non-specific binding;
e. capturing a barcode information on said solid support to said nucleic acid target; and
f. breaking said nucleic acid target into fragments by breaking said strand transfer complexes, wherein at least one fragment attaches to a barcode template on said solid support.

25. A method for tracking nucleic acid fragment origin by barcode tagging comprising:
a. providing a plurality of solid supports having clonal barcode templates or semi-clonal barcode templates immobilized thereon;
b. providing a plurality of transpososomes, each transpososome comprising transposable DNA and transposase, wherein at least one transposable DNA in the transpososome is capable of being captured to said barcode template on said solid support directly or indirectly;
c. contacting a nucleic acid target with said transpososomes to form stable strand transfer complexes;
d. attaching said strand transfer complexes to said solid support via non-specific binding;
e. breaking said nucleic acid target into fragments by breaking said strand transfer complexes and keeping fragments on the solid support by non-specific binding; and
f. capturing a barcode information on said solid support to said nucleic acid fragment, wherein at least one fragment attaches to a barcode template on said solid support.

26. A method for tracking nucleic acid fragment origin by barcode tagging comprising:
   a. providing a plurality of solid supports having clonal barcode templates or semi-clonal barcode templates immobilized thereon;
   b. providing a plurality of transpososomes, each transpososome comprising transposable DNA and transposase, wherein at least one transposable DNA in the transpososome is capable of being captured to said barcode template on said solid support directly or indirectly;
   c. attaching a nucleic acid target to said solid support via non-specific binding;
   d. contacting the non-specifically bound nucleic acid target with said transpososomes to form stable strand transfer complexes on the solid support;
   e. capturing a barcode information on said solid support to said nucleic acid target; and
   f. breaking said nucleic acid target into fragments by breaking said strand transfer complexes, wherein at least one fragment attaches to a barcode template on said solid support.

27. A method for tracking nucleic acid fragment origin by barcode tagging comprising:
   a. providing a plurality of solid supports having clonal barcode templates or semi-clonal barcode templates immobilized thereon;
   b. providing a plurality of transpososomes, each transpososome comprising transposable DNA and transposase, wherein at least one transposable DNA in the transpososome is capable of being captured to said barcode template on said solid support directly or indirectly;
   c. attaching a nucleic acid target to said solid support via non-specific binding;
   d. contacting the non-specifically bound nucleic acid target with said transpososomes to form stable strand transfer complexes on the solid support;
   e. breaking said nucleic acid target into fragments by breaking said strand transfer complexes and keeping fragments on the solid support by non-specific binding; and
   f. capturing a barcode information on said solid support to said nucleic acid fragments, wherein at least one fragment attaches to a barcode template on said solid support.

28. The method of claim 24, wherein said capturing reaction is by ligation, or by hybridization, or by affinity tag, or by antibody and antigen reaction, or by click chemistry, or a combination thereof.

29. A method for determining linkage information of a nucleic acid target comprising:
   a. generating barcode tagged fragments of a nucleic acid target according to claim 1;
   b. determining the sequence of the nucleic acid fragments and the barcodes; and
   c. determining the linkage information of the nucleic acid target based on the barcode sequences when at least two fragments from the same nucleic acid target received identical barcode information.

30. The method of claim 1, wherein said solid support with barcode tagged fragments is further treated with a single strand exonuclease.

31. A method of generating a soluble library of barcode tagged fragments of a nucleic acid target comprising:
   a. generating barcode tagged fragments of a nucleic acid target according to the method of claim 1;
   b. denaturing the barcode tagged fragments, thereby producing a pool of single stranded barcode tagged fragments immobilized on the solid support; and
   c. releasing the barcode tagged nucleic acid fragments from the solid support or copying through primer extension to generate a soluble library.

32. A method of generating a soluble library of barcode tagged fragments of a nucleic acid target comprising:
   a. generating barcode tagged fragments of a nucleic acid target according to the method of claim 1;
   b. repairing a gap produced during transposition reaction between nucleic acid fragment and transposon complementary strand; and
   c. releasing the barcode tagged nucleic acid fragments from the solid support or copying through primer extension or amplification to generate a soluble library.

33. A method of generating a soluble library of barcode tagged fragments of a nucleic acid target comprising:
   a. generating barcode tagged fragments of a nucleic acid target according to the method of claim 1;
   b. providing a transposable DNA and a transposase;
   c. tagging the immobilized barcode tagged fragments with said transposable DNA and transposase to attach an additional sequence; and
   d. releasing the barcode tagged nucleic acid fragments from the solid support via primer extension or amplification to generate a soluble library using at least a primer targeted to the attached additional sequence.

34. A method of generating a soluble library of barcode tagged fragments of a nucleic acid target comprising:
   a. generating barcode tagged fragments of a nucleic acid target according to the method of claim 1;
   b. fragmenting the barcode tagged fragments further physically or enzymatically;
   c. ligating an adaptor sequence to the barcode tagged fragments on the solid support; and
   d. releasing the barcode tagged nucleic acid fragments from the solid support via primer extension or amplification to generate a soluble library using at least a primer targeted to the adaptor sequence ligated to the barcode tagged fragments.

35. The method of claim 31, wherein the primers used in said primer extension or amplification are selected from the group consisting of random degenerate primers, primers for common adaptors, gene specific primers, exome specific primers, and a combination thereof.

36. The method of claim 31, wherein said soluble library is used for sequencing to determine phasing information of the nucleic acid target.

37. The method of claim 31, wherein said soluble library is used for sequencing to determine the identity of duplicated reads.

38. The methods of claim 1, wherein said nucleic acid target comprises a plurality of nucleic acid molecules originated from DNA or RNA in natural, modified, amplified, or other chemically treated forms or in strand transfer complexes.

39. The method of claim 1, wherein the breaking of strand transfer complexes is using protease treatment, high temperature treatment, or a protein denaturing agent, or a combination thereof.

40. The method of claim 14, wherein the ligation is performed using a ligase, and wherein the ligase is selected from the group consisting of DNA ligase, RNA ligase in a wildtype or a mutant or a tagged version thereof, and a combination thereof.

* * * * *